(12) United States Patent
Savage et al.

(10) Patent No.: US 8,583,227 B2
(45) Date of Patent: *Nov. 12, 2013

(54) EVALUATION OF GASTROINTESTINAL FUNCTION USING PORTABLE ELECTROVISCEROGRAPHY SYSTEMS AND METHODS OF USING THE SAME

(75) Inventors: George Savage, Portola Valley, CA (US); Hooman Hafezi, Reedwood City, CA (US); Olivier Colliou, Los Gatos, CA (US); Mark Zdeblick, Portola Valley, CA (US); Angela Strand, Portland, OR (US)

(73) Assignee: Proteus Digital Health, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/243,759

(22) Filed: Sep. 23, 2011

(65) Prior Publication Data

US 2012/0016211 A1    Jan. 19, 2012

Related U.S. Application Data

(63) Continuation of application No. 12/665,022, filed as application No. PCT/US2009/067584 on Dec. 10, 2009, now Pat. No. 8,055,334.

(60) Provisional application No. 61/121,878, filed on Dec. 11, 2008, provisional application No. 61/121,881, filed on Dec. 11, 2008.

(51) Int. Cl.
*A61B 5/05*    (2006.01)
(52) U.S. Cl.
USPC ............................................ 600/547; 607/60

(58) Field of Classification Search
USPC .............................................. 607/60; 600/547
See application file for complete search history.

(56) References Cited

U.S. PATENT DOCUMENTS

| | | | |
|---|---|---|---|
| 3,589,943 A | 6/1971 | Grubb et al. |
| 3,607,788 A | 9/1971 | Adolph |
| 3,642,008 A | 2/1972 | Bolduc |
| 3,679,480 A | 7/1972 | Brown et al. |

(Continued)

FOREIGN PATENT DOCUMENTS

| CN | 1991868 | 7/2007 |
|---|---|---|
| CN | 101005470 | 7/2007 |

(Continued)

OTHER PUBLICATIONS

Barrie, Heidelberg pH capsule gastric analysis. Texbook of Natural Medicine, (1992), Pizzorno, Murray & Barrie.

(Continued)

*Primary Examiner* — Max Hindenburg
*Assistant Examiner* — Renee Danega
(74) *Attorney, Agent, or Firm* — Bozicevic, Field & Francis LLP; Bret E. Field

(57) ABSTRACT

Portable electroviscerography systems are provided. Aspects of the systems include a body-associated receiver and an ingestible identifier unit, both of which are configured to detect visceral electrical signals. The system communicates with an extra-corporeal data processor configured to receive data from the body-associated receiver and generate and electroviscerogram from the received data. Also provided are methods of producing electroviscerograms using systems of the present invention.

16 Claims, 4 Drawing Sheets

(56) References Cited

U.S. PATENT DOCUMENTS

| | | | |
|---|---|---|---|
| 3,682,160 | A | 8/1972 | Murata |
| 3,719,183 | A | 3/1973 | Schwartz |
| 3,799,802 | A | 3/1974 | Schneble, Jr. et al. |
| 3,828,766 | A | 8/1974 | Krasnow |
| 3,837,339 | A | 9/1974 | Aisenberg et al. |
| 3,893,111 | A | 7/1975 | Cotter |
| 3,944,064 | A | 3/1976 | Bashaw et al. |
| 3,967,202 | A | 6/1976 | Batz |
| 3,989,050 | A | 11/1976 | Buchalter |
| 4,017,856 | A | 4/1977 | Wiegand |
| 4,055,178 | A | 10/1977 | Harrigan |
| 4,077,397 | A | 3/1978 | Ellis |
| 4,077,398 | A | 3/1978 | Ellis |
| 4,082,087 | A | 4/1978 | Howson |
| 4,090,752 | A | 5/1978 | Long |
| 4,106,348 | A | 8/1978 | Auphan |
| 4,129,125 | A | 12/1978 | Lester |
| 4,166,453 | A | 9/1979 | McClelland |
| 4,239,046 | A | 12/1980 | Ong |
| 4,251,795 | A | 2/1981 | Shibasaki et al. |
| 4,269,189 | A | 5/1981 | Abraham |
| 4,331,654 | A | 5/1982 | Morris |
| 4,345,588 | A | 8/1982 | Widder et al. |
| 4,418,697 | A | 12/1983 | Tama |
| 4,425,117 | A | 1/1984 | Hugemann et al. |
| 4,494,950 | A | 1/1985 | Fischell |
| 4,559,950 | A | 12/1985 | Vaughan |
| 4,564,363 | A | 1/1986 | Bagnall et al. |
| 4,578,061 | A | 3/1986 | Lemelson |
| 4,635,641 | A | 1/1987 | Hoffman |
| 4,654,165 | A | 3/1987 | Eisenberg |
| 4,663,250 | A | 5/1987 | Ong et al. |
| 4,669,479 | A | 6/1987 | Dunseath |
| 4,681,111 | A | 7/1987 | Silvian |
| 4,725,997 | A | 2/1988 | Urquhart et al. |
| 4,763,659 | A | 8/1988 | Dunseath |
| 4,767,627 | A | 8/1988 | Caldwell et al. |
| 4,784,162 | A | 11/1988 | Ricks |
| 4,793,825 | A | 12/1988 | Benjamin et al. |
| 4,844,076 | A | 7/1989 | Lesho |
| 4,896,261 | A | 1/1990 | Nolan |
| 4,975,230 | A | 12/1990 | Pinkhasov |
| 4,987,897 | A | 1/1991 | Funke |
| 5,016,634 | A | 5/1991 | Vock et al. |
| 5,079,006 | A | 1/1992 | Urquhart |
| 5,167,626 | A | 12/1992 | Casper |
| 5,176,626 | A | 1/1993 | Soehendra |
| 5,261,402 | A | 11/1993 | DiSabito |
| 5,263,481 | A | 11/1993 | Axelgaard et al. |
| 5,279,607 | A | 1/1994 | Schentag et al. |
| 5,281,287 | A | 1/1994 | Lloyd |
| 5,283,136 | A | 2/1994 | Peled et al. |
| 5,305,745 | A | 4/1994 | Zacouto |
| 5,318,557 | A | 6/1994 | Gross |
| 5,394,882 | A | 3/1995 | Mawhinney |
| 5,395,366 | A | 3/1995 | D'Andrea et al. |
| 5,436,091 | A | 7/1995 | Shackle et al. |
| 5,443,461 | A | 8/1995 | Atkinson et al. |
| 5,443,843 | A | 8/1995 | Curatolo et al. |
| 5,458,141 | A | 10/1995 | Neil et al. |
| 5,485,841 | A | 1/1996 | Watkin et al. |
| 5,511,548 | A | 4/1996 | Riazzi et al. |
| 5,567,210 | A | 10/1996 | Bates et al. |
| 5,596,302 | A | 1/1997 | Mastrocola et al. |
| 5,600,548 | A | 2/1997 | Nguyen et al. |
| 5,634,466 | A | 6/1997 | Gruner |
| 5,634,468 | A | 6/1997 | Platt |
| 5,645,063 | A | 7/1997 | Straka et al. |
| 5,705,189 | A | 1/1998 | Lehmann et al. |
| 5,720,771 | A | 2/1998 | Snell |
| 5,738,708 | A | 4/1998 | Peachey et al. |
| 5,740,811 | A | 4/1998 | Hedberg |
| 5,757,326 | A | 5/1998 | Koyama et al. |
| 5,792,048 | A | 8/1998 | Schaefer |
| 5,802,467 | A | 9/1998 | Salazar |
| 5,833,716 | A | 11/1998 | Bar-Or |
| 5,845,265 | A | 12/1998 | Woolston |
| 5,862,803 | A | 1/1999 | Besson |
| 5,862,808 | A | 1/1999 | Albarello |
| 5,868,136 | A | 2/1999 | Fox |
| 5,921,925 | A | 7/1999 | Cartmell et al. |
| 5,925,030 | A | 7/1999 | Gross et al. |
| 5,925,066 | A | 7/1999 | Kroll et al. |
| 5,957,854 | A | 9/1999 | Besson |
| 5,963,132 | A | 10/1999 | Yoakum et al. |
| 5,974,124 | A | 10/1999 | Schlueter, Jr. et al. |
| 5,981,166 | A | 11/1999 | Mandecki |
| 5,999,846 | A | 12/1999 | Pardey et al. |
| 6,023,631 | A | 2/2000 | Cartmell et al. |
| 6,038,464 | A | 3/2000 | Axelgaard et al. |
| 6,042,710 | A | 3/2000 | Dubrow |
| 6,047,203 | A | 4/2000 | Sackner |
| 6,076,016 | A | 6/2000 | Feierbach et al. |
| 6,081,734 | A | 6/2000 | Batz |
| 6,083,248 | A | 7/2000 | Thompson |
| 6,091,975 | A | 7/2000 | Daddona et al. |
| 6,095,985 | A | 8/2000 | Raymond et al. |
| 6,115,636 | A | 9/2000 | Ryan |
| 6,122,351 | A | 9/2000 | Schlueter, Jr. et al. |
| 6,141,592 | A | 10/2000 | Pauly |
| 6,200,265 | B1 | 3/2001 | Walsh et al. |
| 6,204,764 | B1 | 3/2001 | Maloney |
| 6,206,702 | B1 | 3/2001 | Hayden et al. |
| 6,217,744 | B1 | 4/2001 | Crosby |
| 6,231,593 | B1 | 5/2001 | Meserol |
| 6,245,057 | B1 | 6/2001 | Sieben et al. |
| 6,269,058 | B1 | 7/2001 | Yamanoi et al. |
| 6,275,476 | B1 | 8/2001 | Wood |
| 6,285,897 | B1 | 9/2001 | Kilcoyne et al. |
| 6,287,252 | B1 | 9/2001 | Lugo |
| 6,288,629 | B1 | 9/2001 | Cofino et al. |
| 6,289,238 | B1 | 9/2001 | Besson |
| 6,315,719 | B1 | 11/2001 | Rode et al. |
| 6,342,774 | B1 | 1/2002 | Kreisinger et al. |
| 6,358,202 | B1 | 3/2002 | Arent |
| 6,364,834 | B1 | 4/2002 | Reuss |
| 6,366,206 | B1 | 4/2002 | Ishikawa et al. |
| 6,368,190 | B1 | 4/2002 | Easter et al. |
| 6,371,927 | B1 | 4/2002 | Brune |
| 6,374,670 | B1 | 4/2002 | Spelman |
| 6,380,858 | B1 | 4/2002 | Yarin et al. |
| 6,394,997 | B1 | 5/2002 | Lemelson |
| 6,409,674 | B1 | 6/2002 | Brockway et al. |
| 6,426,863 | B1 | 7/2002 | Munshi |
| 6,432,292 | B1 | 8/2002 | Pinto et al. |
| 6,440,069 | B1 | 8/2002 | Raymond et al. |
| 6,441,747 | B1 | 8/2002 | Khair |
| 6,453,199 | B1 | 9/2002 | Kobozev |
| 6,477,424 | B1 | 11/2002 | Thompson et al. |
| 6,494,829 | B1 | 12/2002 | New et al. |
| 6,496,705 | B1 | 12/2002 | Ng et al. |
| 6,526,315 | B1 | 2/2003 | Inagawa |
| 6,531,026 | B1 | 3/2003 | Takeichi et al. |
| 6,544,174 | B2 | 4/2003 | West |
| 6,564,079 | B1 | 5/2003 | Cory |
| 6,572,636 | B1 | 6/2003 | Hagen et al. |
| 6,577,893 | B1 | 6/2003 | Besson |
| 6,579,231 | B1 | 6/2003 | Phipps |
| 6,595,929 | B2 | 7/2003 | Stivoric |
| 6,605,038 | B1 | 8/2003 | Teller |
| 6,609,018 | B2 | 8/2003 | Cory |
| 6,612,984 | B1 | 9/2003 | Kerr |
| 6,632,175 | B1 | 10/2003 | Marshall |
| 6,632,216 | B2 | 10/2003 | Houzego et al. |
| 6,635,279 | B2 | 10/2003 | Kolter et al. |
| 6,643,541 | B2 | 11/2003 | Mok et al. |
| 6,654,638 | B1 | 11/2003 | Sweeney |
| 6,663,846 | B1 | 12/2003 | McCombs |
| 6,673,474 | B2 | 1/2004 | Yamamoto |
| 6,680,923 | B1 | 1/2004 | Leon |
| 6,689,117 | B2 | 2/2004 | Sweeney et al. |
| 6,694,161 | B2 | 2/2004 | Mehrotra |
| 6,704,602 | B2 | 3/2004 | Berg et al. |
| 6,720,923 | B1 | 4/2004 | Hayward et al. |

(56) References Cited

U.S. PATENT DOCUMENTS

| | | |
|---|---|---|
| 6,738,671 B2 | 5/2004 | Christophersom et al. |
| 6,740,033 B1 | 5/2004 | Olejniczak et al. |
| 6,745,082 B2 | 6/2004 | Axelgaard et al. |
| 6,755,783 B2 | 6/2004 | Cosentino |
| 6,757,523 B2 | 6/2004 | Fry |
| 6,759,968 B2 | 7/2004 | Zierolf |
| 6,800,060 B2 | 10/2004 | Marshall |
| 6,801,137 B2 | 10/2004 | Eggers et al. |
| 6,814,706 B2 | 11/2004 | Barton et al. |
| 6,822,554 B2 | 11/2004 | Vrijens et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,845,272 B1 | 1/2005 | Thomsen |
| 6,864,780 B2 | 3/2005 | Doi |
| 6,879,810 B2 | 4/2005 | Bouet |
| 6,882,881 B1 | 4/2005 | Lesser et al. |
| 6,897,788 B2 | 5/2005 | Khair et al. |
| 6,909,878 B2 | 6/2005 | Haller |
| 6,922,592 B2 | 7/2005 | Thompson et al. |
| 6,928,370 B2 | 8/2005 | Anuzis et al. |
| 6,929,636 B1 | 8/2005 | Von Alten |
| 6,937,150 B2 | 8/2005 | Medema |
| 6,942,616 B2 | 9/2005 | Kerr |
| 6,951,536 B2 | 10/2005 | Yokoi |
| 6,957,107 B2 | 10/2005 | Rogers et al. |
| 6,959,929 B2 | 11/2005 | Pugnet et al. |
| 6,968,153 B1 | 11/2005 | Heinonen |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,044,911 B2 | 5/2006 | Drinan et al. |
| 7,046,649 B2 | 5/2006 | Awater et al. |
| 7,118,531 B2 | 10/2006 | Krill |
| 7,127,300 B2 | 10/2006 | Mazar et al. |
| 7,146,228 B2 | 12/2006 | Nielsen |
| 7,146,449 B2 | 12/2006 | Do et al. |
| 7,149,581 B2 | 12/2006 | Goedeke et al. |
| 7,154,071 B2 | 12/2006 | Sattler et al. |
| 7,155,232 B2 | 12/2006 | Godfrey et al. |
| 7,160,258 B2 | 1/2007 | Imran |
| 7,161,484 B2 | 1/2007 | Tsoukalis |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,176,784 B2 | 2/2007 | Gilbert et al. |
| 7,187,960 B2 | 3/2007 | Abreu |
| 7,188,767 B2 | 3/2007 | Penuela |
| 7,194,038 B1 | 3/2007 | Inkinen |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,285,090 B2 | 10/2007 | Stivoric et al. |
| 7,289,855 B2 | 10/2007 | Nghiem |
| 7,291,497 B2 | 11/2007 | Holmes |
| 7,292,139 B2 | 11/2007 | Mazar et al. |
| 7,294,105 B1 | 11/2007 | Islam |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,368,190 B2 | 5/2008 | Heller et al. |
| 7,368,191 B2 | 5/2008 | Andelman et al. |
| 7,373,196 B2 | 5/2008 | Ryu et al. |
| 7,375,739 B2 | 5/2008 | Robbins |
| 7,376,435 B2 | 5/2008 | McGowan |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1 | 8/2008 | Kroll et al. |
| 7,414,543 B2 | 8/2008 | Rye et al. |
| 8,224,667 B1 | 8/2008 | Rye et al. |
| 7,424,268 B2 | 9/2008 | Diener |
| 7,424,319 B2 | 9/2008 | Muehlsteff |
| 7,427,266 B2 | 9/2008 | Ayer et al. |
| 7,471,665 B2 | 12/2008 | Perlman |
| 7,499,674 B2 | 3/2009 | Salokannel |
| 7,502,643 B2 | 3/2009 | Farringdon et al. |
| 7,505,795 B1 | 3/2009 | Lim et al. |
| 7,510,121 B2 | 3/2009 | Koenck |
| 7,512,448 B2 | 3/2009 | Malick |
| 7,515,043 B2 | 4/2009 | Welch |
| 7,519,416 B2 | 4/2009 | Sula et al. |
| 7,523,756 B2 | 4/2009 | Minai |
| 7,525,426 B2 | 4/2009 | Edelstein |
| 7,539,533 B2 | 5/2009 | Tran |
| 7,542,878 B2 | 6/2009 | Nanikashvili |
| 7,551,590 B2 | 6/2009 | Haller |
| 7,554,452 B2 | 6/2009 | Cole |
| 7,575,005 B2 | 8/2009 | Mumford |
| 7,616,111 B2 | 11/2009 | Covannon |
| 7,617,001 B2 | 11/2009 | Penner et al. |
| 7,639,473 B2 | 12/2009 | Hsu et al. |
| 7,640,802 B2 | 1/2010 | King et al. |
| 7,647,112 B2 | 1/2010 | Tracey |
| 7,647,185 B2 | 1/2010 | Tarassenko et al. |
| 7,653,031 B2 | 1/2010 | Godfrey et al. |
| 7,668,437 B1 | 2/2010 | Yamada et al. |
| 7,672,703 B2 | 3/2010 | Yeo et al. |
| 7,672,714 B2 | 3/2010 | Kuo |
| 7,673,679 B2 | 3/2010 | Harrison et al. |
| 7,678,043 B2 | 3/2010 | Gilad |
| 7,689,437 B1 | 3/2010 | Teller et al. |
| 7,697,994 B2 | 4/2010 | VanDanacker et al. |
| 7,720,036 B2 | 5/2010 | Sadri |
| 7,729,776 B2 | 6/2010 | Von Arx et al. |
| 7,733,224 B2 | 6/2010 | Tran |
| 7,736,318 B2 | 6/2010 | Cosentino |
| 7,756,587 B2 | 7/2010 | Penner et al. |
| 7,796,043 B2 | 9/2010 | Euliano et al. |
| 7,797,033 B2 | 9/2010 | D'Andrea et al. |
| 7,809,399 B2 | 10/2010 | Lu |
| 7,844,341 B2 | 11/2010 | Von Arx et al. |
| 7,904,133 B2 | 3/2011 | Gehman et al. |
| 8,073,707 B2 | 12/2011 | Teller et al. |
| 8,083,128 B2 | 12/2011 | Dembo et al. |
| 8,123,576 B2 | 2/2012 | Kim |
| 8,180,425 B2 | 5/2012 | Selvitelli et al. |

(56) References Cited

U.S. PATENT DOCUMENTS

| | | |
|---|---|---|
| 8,200,320 B2 | 6/2012 | Kovacs |
| 8,214,007 B2 | 7/2012 | Baker et al. |
| 8,238,998 B2 | 8/2012 | Park |
| 8,249,686 B2 | 8/2012 | Libbus et al. |
| 8,258,962 B2 | 9/2012 | Robertson et al. |
| 8,285,356 B2 | 10/2012 | Bly et al. |
| 8,290,574 B2 | 10/2012 | Feild et al. |
| 8,301,232 B2 | 10/2012 | Albert et al. |
| 8,308,640 B2 | 11/2012 | Baldus et al. |
| 8,315,687 B2 | 11/2012 | Cross et al. |
| 8,369,936 B2 | 2/2013 | Farringdon et al. |
| 8,386,009 B2 | 2/2013 | Lindberg et al. |
| 2001/0027331 A1 | 10/2001 | Thompson |
| 2001/0044588 A1 | 11/2001 | Mault |
| 2001/0051766 A1 | 12/2001 | Gazdzinski |
| 2002/0002326 A1 | 1/2002 | Causey, III |
| 2002/0026111 A1 | 2/2002 | Ackerman |
| 2002/0032385 A1 | 3/2002 | Raymond et al. |
| 2002/0040278 A1 | 4/2002 | Anuzis et al. |
| 2002/0077620 A1 | 6/2002 | Sweeney et al. |
| 2002/0132226 A1 | 9/2002 | Nair |
| 2002/0192159 A1 | 12/2002 | Reitberg |
| 2002/0193669 A1 | 12/2002 | Glukhovsky |
| 2002/0193846 A1 | 12/2002 | Pool et al. |
| 2002/0198470 A1 | 12/2002 | Imran et al. |
| 2003/0017826 A1 | 1/2003 | Fishman |
| 2003/0023150 A1 | 1/2003 | Yokoi et al. |
| 2003/0028226 A1 | 2/2003 | Thompson |
| 2003/0063522 A1 | 4/2003 | Sagar |
| 2003/0065536 A1 | 4/2003 | Hansen |
| 2003/0076179 A1 | 4/2003 | Branch et al. |
| 2003/0083559 A1 | 5/2003 | Thompson |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0181815 A1 | 9/2003 | Ebner et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2004/0008123 A1 | 1/2004 | Carrender et al. |
| 2004/0018476 A1 | 1/2004 | LaDue |
| 2004/0019172 A1 | 1/2004 | Yang et al. |
| 2004/0034295 A1 | 2/2004 | Salganicoff |
| 2004/0049245 A1 | 3/2004 | Gass |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0115517 A1 | 6/2004 | Fukada et al. |
| 2004/0121015 A1 | 6/2004 | Chidlaw et al. |
| 2004/0148140 A1 | 7/2004 | Tarassenko et al. |
| 2004/0153007 A1 | 8/2004 | Harris |
| 2004/0162501 A1* | 8/2004 | Imran ............ 600/547 |
| 2004/0167226 A1 | 8/2004 | Serafini |
| 2004/0167801 A1 | 8/2004 | Say et al. |
| 2004/0193020 A1 | 9/2004 | Chiba |
| 2004/0193029 A1 | 9/2004 | Glukhovsky |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0260154 A1 | 12/2004 | Sidelnik |
| 2005/0017841 A1 | 1/2005 | Doi |
| 2005/0020887 A1 | 1/2005 | Goldberg |
| 2005/0021103 A1 | 1/2005 | DiLorenzo |
| 2005/0021370 A1 | 1/2005 | Riff |
| 2005/0024198 A1 | 2/2005 | Ward |
| 2005/0027205 A1 | 2/2005 | Tarassenko et al. |
| 2005/0038321 A1 | 2/2005 | Fujita et al. |
| 2005/0043634 A1 | 2/2005 | Yokoi et al. |
| 2005/0043894 A1 | 2/2005 | Fernandez |
| 2005/0054897 A1 | 3/2005 | Hashimoto et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0090753 A1 | 4/2005 | Goor et al. |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0137480 A1 | 6/2005 | Alt et al. |
| 2005/0143623 A1 | 6/2005 | Kojima |
| 2005/0148883 A1 | 7/2005 | Boesen |
| 2005/0151625 A1 | 7/2005 | Lai |
| 2005/0154428 A1 | 7/2005 | Bruinsma |
| 2005/0156709 A1 | 7/2005 | Gilbert et al. |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0245839 A1 | 11/2005 | Stivoric et al. |
| 2005/0259768 A1 | 11/2005 | Yang et al. |
| 2005/0261559 A1 | 11/2005 | Mumford |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0028727 A1 | 2/2006 | Moon et al. |
| 2006/0036134 A1 | 2/2006 | Tarassenko et al. |
| 2006/0058602 A1 | 3/2006 | Kwiatkowski et al. |
| 2006/0061472 A1 | 3/2006 | Lovoi et al. |
| 2006/0065713 A1 | 3/2006 | Kingery |
| 2006/0068006 A1 | 3/2006 | Begleiter |
| 2006/0074283 A1 | 4/2006 | Henderson |
| 2006/0078765 A1 | 4/2006 | Yang et al. |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122667 A1 | 6/2006 | Chavan et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |

(56) References Cited

U.S. PATENT DOCUMENTS

| | | |
|---|---|---|
| 2006/0155174 A1 | 7/2006 | Glukhovsky et al. |
| 2006/0155183 A1 | 7/2006 | Kroecker |
| 2006/0158820 A1 | 7/2006 | Takiguchi |
| 2006/0161225 A1 | 7/2006 | Sormann et al. |
| 2006/0179949 A1 | 8/2006 | Kim |
| 2006/0183992 A1 | 8/2006 | Kawashima |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0229053 A1 | 10/2006 | Sivard |
| 2006/0235489 A1 | 10/2006 | Drew |
| 2006/0243288 A1 | 11/2006 | Kim et al. |
| 2006/0247505 A1 | 11/2006 | Siddiqui |
| 2006/0253005 A1 | 11/2006 | Drinan |
| 2006/0265246 A1 | 11/2006 | Hoag |
| 2006/0270346 A1 | 11/2006 | Ibrahim |
| 2006/0273882 A1 | 12/2006 | Posamentier |
| 2006/0276702 A1 | 12/2006 | McGinnis |
| 2006/0280227 A1 | 12/2006 | Pinkney |
| 2006/0282001 A1 | 12/2006 | Noel |
| 2006/0289640 A1 | 12/2006 | Mercure |
| 2006/0293607 A1 | 12/2006 | Alt |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0060800 A1 | 3/2007 | Drinan et al. |
| 2007/0073353 A1 | 3/2007 | Rooney et al. |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135691 A1 | 6/2007 | Zingelewicz et al. |
| 2007/0135803 A1 | 6/2007 | Belson |
| 2007/0142721 A1 | 6/2007 | Berner et al. |
| 2007/0156016 A1 | 7/2007 | Betesh |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0179371 A1 | 8/2007 | Peyser et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0299480 A1 | 12/2007 | Hill |
| 2008/0014866 A1 | 1/2008 | Lipowski |
| 2008/0015421 A1 | 1/2008 | Penner |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0039700 A1 | 2/2008 | Drinan et al. |
| 2008/0045843 A1 | 2/2008 | Tsuji et al. |
| 2008/0046038 A1 | 2/2008 | Hill |
| 2008/0051647 A1 | 2/2008 | Wu et al. |
| 2008/0051667 A1 | 2/2008 | Goldreich |
| 2008/0051767 A1 | 2/2008 | Rossing et al. |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Boric-Lubecke |
| 2008/0077028 A1 | 3/2008 | Schaldach et al. |
| 2008/0077188 A1 | 3/2008 | Denker et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks et al. |
| 2008/0103440 A1 | 5/2008 | Ferren et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0121825 A1 | 5/2008 | Trovato et al. |
| 2008/0137566 A1 | 6/2008 | Marholev |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBoeuf |
| 2008/0154104 A1 | 6/2008 | Lamego |
| 2008/0166992 A1 | 7/2008 | Ricordi |
| 2008/0175898 A1 | 7/2008 | Jones et al. |
| 2008/0183245 A1 | 7/2008 | Van Oort |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214985 A1 | 9/2008 | Yanaki |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0281636 A1 | 11/2008 | Jung et al. |
| 2008/0284599 A1* | 11/2008 | Zdeblick et al. ........... 340/572.1 |
| 2008/0288026 A1 | 11/2008 | Cross et al. |
| 2008/0294020 A1 | 11/2008 | Sapounas |
| 2008/0299197 A1 | 12/2008 | Toneguzzo et al. |
| 2008/0300572 A1 | 12/2008 | Rankers |
| 2008/0303638 A1 | 12/2008 | Nguyen |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0311852 A1 | 12/2008 | Hansen |
| 2008/0312522 A1 | 12/2008 | Rowlandson |
| 2008/0316020 A1 | 12/2008 | Robertson |
| 2009/0009330 A1 | 1/2009 | Sakama et al. |
| 2009/0009332 A1 | 1/2009 | Nunez et al. |
| 2009/0024045 A1 | 1/2009 | Prakash |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0062634 A1 | 3/2009 | Say et al. |
| 2009/0062670 A1 | 3/2009 | Sterling |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0076340 A1 | 3/2009 | Libbus et al. |
| 2009/0076343 A1 | 3/2009 | James |
| 2009/0076397 A1 | 3/2009 | Libbus et al. |
| 2009/0082645 A1 | 3/2009 | Hafezi et al. |
| 2009/0087483 A1 | 4/2009 | Sison |
| 2009/0088618 A1 | 4/2009 | Arneson |
| 2009/0099435 A1 | 4/2009 | Say et al. |
| 2009/0105561 A1 | 4/2009 | Boyden et al. |
| 2009/0110148 A1 | 4/2009 | Zhang |

(56) References Cited

U.S. PATENT DOCUMENTS

| | | |
|---|---|---|
| 2009/0112626 A1 | 4/2009 | Talbot |
| 2009/0124871 A1 | 5/2009 | Arshak |
| 2009/0131774 A1 | 5/2009 | Sweitzer |
| 2009/0135886 A1 | 5/2009 | Robertson et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0227988 A1 | 9/2009 | Wood et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0253960 A1 | 10/2009 | Takenaka et al. |
| 2009/0256702 A1 | 10/2009 | Robertson |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0281539 A1 | 11/2009 | Selig |
| 2009/0292194 A1 | 11/2009 | Libbus et al. |
| 2009/0295548 A1 | 12/2009 | Ronkka |
| 2009/0296677 A1 | 12/2009 | Mahany |
| 2009/0303920 A1 | 12/2009 | Mahany |
| 2009/0306633 A1 | 12/2009 | Trovato et al. |
| 2009/0312619 A1 | 12/2009 | Say et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0001841 A1 | 1/2010 | Cardullo |
| 2010/0006585 A1 | 1/2010 | Flowers et al. |
| 2010/0010330 A1 | 1/2010 | Rankers |
| 2010/0049004 A1 | 2/2010 | Edman et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0069717 A1 | 3/2010 | Hafezi et al. |
| 2010/0081894 A1 | 4/2010 | Zdeblick et al. |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0106001 A1 | 4/2010 | Say et al. |
| 2010/0118853 A1 | 5/2010 | Godfrey |
| 2010/0139672 A1 | 6/2010 | Kroll et al. |
| 2010/0160742 A1 | 6/2010 | Seidl et al. |
| 2010/0168659 A1 | 7/2010 | Say et al. |
| 2010/0179398 A1 | 7/2010 | Say et al. |
| 2010/0185055 A1 | 7/2010 | Robertson |
| 2010/0191073 A1 | 7/2010 | Tarassenko et al. |
| 2010/0210299 A1 | 8/2010 | Gorbachov |
| 2010/0222652 A1 | 9/2010 | Cho |
| 2010/0228113 A1 | 9/2010 | Solosko |
| 2010/0234706 A1 | 9/2010 | Gilland |
| 2010/0234715 A1 | 9/2010 | Shin |
| 2010/0234914 A1 | 9/2010 | Shen |
| 2010/0245091 A1 | 9/2010 | Singh |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0274111 A1 | 10/2010 | Say et al. |
| 2010/0280345 A1 | 11/2010 | Say et al. |
| 2010/0280346 A1 | 11/2010 | Say et al. |
| 2010/0295694 A1 | 11/2010 | Kauffman et al. |
| 2010/0298668 A1 | 11/2010 | Hafezi et al. |
| 2010/0298730 A1 | 11/2010 | Tarassenko et al. |
| 2010/0299155 A1 | 11/2010 | Findlay et al. |
| 2010/0312188 A1 | 12/2010 | Robertson et al. |
| 2010/0312580 A1 | 12/2010 | Tarassenko et al. |
| 2010/0332443 A1 | 12/2010 | Gartenberg |
| 2011/0009715 A1 | 1/2011 | O'Reilly et al. |
| 2011/0040203 A1 | 2/2011 | Savage et al. |
| 2011/0050431 A1 | 3/2011 | Hood et al. |
| 2011/0054265 A1 | 3/2011 | Hafezi et al. |
| 2011/0065983 A1 | 3/2011 | Hafezi et al. |
| 2011/0077660 A1 | 3/2011 | Janik et al. |
| 2011/0105864 A1 | 5/2011 | Robertson et al. |
| 2011/0124983 A1 | 5/2011 | Kroll et al. |
| 2011/0144470 A1 | 6/2011 | Mazar et al. |
| 2011/0224912 A1 | 9/2011 | Bhavaraju et al. |
| 2011/0230732 A1 | 9/2011 | Edman et al. |
| 2011/0279963 A1 | 11/2011 | Kumar et al. |
| 2012/0029309 A1 | 2/2012 | Paquet et al. |
| 2012/0062371 A1 | 3/2012 | Radivojevic et al. |

(56) References Cited

U.S. PATENT DOCUMENTS

| | | | |
|---|---|---|---|
| 2012/0101396 A1 | 4/2012 | Solosko et al. |
| 2012/0197144 A1 | 8/2012 | Christ et al. |
| 2012/0265544 A1 | 10/2012 | Hwang et al. |
| 2012/0310070 A1 | 12/2012 | Kumar et al. |
| 2012/0316413 A1 | 12/2012 | Liu et al. |
| 2013/0030259 A1 | 1/2013 | Thomsen et al. |
| 2013/0060115 A1 | 3/2013 | Gehman et al. |

FOREIGN PATENT DOCUMENTS

| | | |
|---|---|---|
| CN | 201076456 | 6/2008 |
| EP | 1246356 | 10/2002 |
| EP | 15434054 | 5/2005 |
| EP | 1702553 | 9/2006 |
| EP | 1789128 | 5/2007 |
| EP | 2143369 | 1/2010 |
| GB | 2432862 | 6/2007 |
| JP | 61017949 | 1/1986 |
| JP | 05-228128 | 9/1993 |
| JP | 10-14898 | 1/1998 |
| JP | 2000-506410 | 5/2000 |
| JP | 2002291684 | 10/2002 |
| JP | 2004-7187 | 1/2004 |
| JP | 2004134384 | 4/2004 |
| JP | 2005-073886 | 3/2005 |
| JP | 2005-087552 | 4/2005 |
| JP | 2005-304880 | 4/2005 |
| JP | 2005-532841 | 11/2005 |
| JP | 2005-532849 | 11/2005 |
| JP | 2006509574 | 3/2006 |
| JP | 2006-177699 | 7/2006 |
| JP | 2006-187611 | 7/2006 |
| JP | 2006278091 | 10/2006 |
| JP | 2007-313340 | 12/2007 |
| JP | 2009-061236 | 3/2009 |
| KR | 20020015907 | 3/2002 |
| KR | 20020061744 | 7/2002 |
| KR | 927471 | 11/2009 |
| TW | 553735 | 9/2003 |
| TW | 200724094 | 7/2007 |
| WO | 8802237 | 4/1988 |
| WO | WO9221307 | 12/1992 |
| WO | WO9308734 | 5/1993 |
| WO | WO9319667 | 10/1993 |
| WO | WO9843537 | 10/1998 |
| WO | WO9937290 | 7/1999 |
| WO | WO9959465 | 11/1999 |
| WO | WO0033246 | 6/2000 |
| WO | WO0100085 | 1/2001 |
| WO | WO0147466 | 7/2001 |
| WO | WO0149364 | 7/2001 |
| WO | WO0174011 | 10/2001 |
| WO | WO0180731 | 11/2001 |
| WO | WO0204406 | 1/2002 |
| WO | WO0245489 | 6/2002 |
| WO | WO02058330 | 7/2002 |
| WO | WO02062276 | 8/2002 |
| WO | WO02087681 | 11/2002 |
| WO | WO03050643 | 6/2003 |
| WO | WO03068061 | 8/2003 |
| WO | WO2004014225 | 2/2004 |
| WO | WO2004019172 | 3/2004 |
| WO | WO2004039256 | 5/2004 |
| WO | WO2004066833 | 8/2004 |
| WO | WO2004066834 | 8/2004 |
| WO | WO2004066903 | 8/2004 |
| WO | WO2004068748 | 8/2004 |
| WO | WO2004068881 | 8/2004 |
| WO | WO2004075751 | 9/2004 |
| WO | WO2004109316 | 12/2004 |
| WO | WO2005011237 | 2/2005 |
| WO | WO2005020023 | 3/2005 |
| WO | WO2005024687 | 3/2005 |
| WO | WO2005047837 | 5/2005 |
| WO | WO2005051166 | 6/2005 |
| WO | WO2005110238 | 11/2005 |
| WO | WO2006021932 | 3/2006 |
| WO | WO2006027586 | 3/2006 |
| WO | WO2006035351 | 4/2006 |
| WO | WO2006055892 | 5/2006 |
| WO | WO2006055956 | 5/2006 |
| WO | WO2006075016 | 7/2006 |
| WO | WO2006100620 | 9/2006 |
| WO | WO2006104843 | 10/2006 |
| WO | WO2006109072 | 10/2006 |
| WO | WO 2006/116718 | * 11/2006 |
| WO | WO2006116718 | 11/2006 |
| WO | WO2006119345 | 11/2006 |
| WO | WO2006127355 | 11/2006 |
| WO | WO2007001724 | 1/2007 |
| WO | WO2007001742 | 1/2007 |
| WO | WO2007013952 | 2/2007 |
| WO | WO2007014084 | 2/2007 |
| WO | WO2007014527 | 2/2007 |
| WO | WO2007021496 | 2/2007 |
| WO | WO2007027660 | 3/2007 |
| WO | WO2007028035 | 3/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007071180 | 6/2007 |
| WO | WO2007096810 | 8/2007 |
| WO | WO2007101141 | 9/2007 |
| WO | WO2007120946 | 10/2007 |
| WO | WO2007127316 | 11/2007 |
| WO | WO2007127879 | 11/2007 |
| WO | WO2007128165 | 11/2007 |
| WO | WO2007130491 | 11/2007 |
| WO | WO2007143535 | 12/2007 |
| WO | WO2007149546 | 12/2007 |
| WO | WO2008008281 | 1/2008 |
| WO | WO2008030482 | 3/2008 |
| WO | WO2008052136 | 5/2008 |
| WO | WO2008063626 | 5/2008 |
| WO | WO2008066617 | 6/2008 |
| WO | WO2008076464 | 6/2008 |
| WO | WO2008089232 | 7/2008 |
| WO | WO2008091683 | 7/2008 |
| WO | WO2008095183 | 8/2008 |
| WO | WO2008097652 | 8/2008 |
| WO | WO2008101107 | 8/2008 |
| WO | WO2008112577 | 9/2008 |
| WO | WO2008112578 | 9/2008 |
| WO | WO2008120156 | 10/2008 |
| WO | WO2008133394 | 11/2008 |
| WO | WO2008134185 | 11/2008 |
| WO | WO2008150633 | 12/2008 |
| WO | WO2009001108 | 12/2008 |
| WO | WO2009006615 | 1/2009 |
| WO | WO2009029453 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010000085 | 1/2010 |
| WO | WO2010009100 | 1/2010 |
| WO | WO2010011833 | 1/2010 |
| WO | WO2010019778 | 2/2010 |
| WO | WO2010057049 | 5/2010 |
| WO | WO2010080765 | 7/2010 |
| WO | WO2010080843 | 7/2010 |
| WO | WO2010107563 | 9/2010 |
| WO | WO2010132331 | 11/2010 |
| WO | WO2010135516 | 11/2010 |
| WO | WO2011068963 | 6/2011 |
| WO | WO2011159336 | 12/2011 |
| WO | WO2011159337 | 12/2011 |
| WO | WO2011159338 | 12/2011 |

(56) References Cited

FOREIGN PATENT DOCUMENTS

| WO | WO2011159339 | 12/2011 |
|----|--------------|---------|
| WO | WO2012104657 | 8/2012 |
| WO | WO2012158190 | 11/2012 |

OTHER PUBLICATIONS

Carlson et al., "Evaluation of a non-invasive respiratory monitoring system for sleeping subjects" Physiological Measurement (1999) 20(1): 53.
Heydari et al., "Analysis of the PLL jitter due to power/ground and substrate noise"; IEEE Transactions on Circuits and Systems (2004) 51(12): 2404-16.
Intromedic, MicroCam Innovative Capsule Endoscope Pamphlet. (2006) 8 pp (http://www.intromedic.com/en/product/productinfo.asp).
MacKay et al., "Radio Telemetering from within the Body Inside Information is Revealed by Tiny Transmitters that can be Swallowed or Implanted in Man or Animal Science" (1991) 1196-1202; 134; American Association for the Advancement of Science, Washington D.C.
Mackay et al., "Endoradiosonde" Nature, (1957) 1239-1240, 179 Nature Publishing Group.
McKenzie et al., "Validation of a new telemetric core temperature monitor" J. Therm. Biol. (2004) 29(7-8):605-11.
Minimitter Co. Inc. "Actiheart" Traditional 510(k) Summary. Sep. 27, 2005.
Minimitter Co. Inc. Noninvasive technology to help your studies succeed. Mini Mitter.com Mar. 31, 2009.
Mini Mitter Co, Inc. 510(k) Premarket Notification Mini-Logger for Diagnostic Spirometer. 9-21 (1999).
Mini Mitter Co, Inc. 510(k) Premarket Notification for VitalSense. Apr. 22, 2004.
Minimitter Co. Inc. VitalSense Integrated Physiological Monitoring System. Product Description. (2005).
Minimitter Co. Inc. VitalSense Wireless Vital Signs Monitoring. Temperatures.com Mar. 31, 2009.
Mohaverian et al., "Estimation of gastric residence time of the Heidelberg capsule in humans: effect of varying food composition" Gastroenterology (1985) 89:(2): 392-7.
Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.
Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.
Tatbul et al., "Confidence-based data management for personal area sensor networks" ACM International Conference Proceeding Series (2004) 72.
Xiaoming et al., "A telemedicine system for wireless home healthcare based on bluetooth and the internet" Telemedicine Journal and e-health (2004) 10(S2): S110-6.
Yang et al., "Fast-switching frequency synthesizer with a discriminator-aided phase detector" IEEE Journal of Solid-State Circuits (2000) 35(10): 1445-52.
Yao et al., "Low Power Digital Communication in Implantable Devices Using Volume Conduction of Biological Tissues" Proceedings of the 28th IEEE, EMBS Annual International Conference, Aug. 30-Sep. 3, 2006.
Zimmerman, "Personal Area Networks: Near-field intrabody communication" IBM Systems Journal (1996) 35 (3-4):609-17.
Zworkin, "A Radio Pill" Nature, (1957) 898, 179 Nature Publishing Group.
Li, P-Y, et al. "An electrochemical intraocular drug delivery device", Sensors and Actuators A 143 (2008) p. 41-48.
NPL_AntennaBasics.pdf, Radio Antennae, http://www.erikdeman.de/html/sail018h.htm; (2008) 3pp.

Santini, J.T. et al, "Microchips as controlled drug delivery-devices", Agnew. Chem. Int. Ed. (2000), vol. 39, p. 2396-2407.
Shawgo, R.S. et al. "BioMEMS from drug delivery", Current Opinion in Solid State and Material Science 6 (2002), p. 329-334.
Soper, S.A. et al. "Bio-Mems Technologies and Applications", Chapter 12, "MEMS for Drug Delivery", p. 325-346 (2007).
Tierney, M.J. et al "Electroreleasing Composite Membranes for Delivery of Insulin and other Biomacromolecules", J. Electrochem. Soc., vol. 137, No. 6, Jun. 1990, p. 2005-2006.
Description of ePatch Technology Platform for ECG and EMG, located it http://www.madebydelta.com/imported/images/DELTA_Web/documents/ME/ePatch_ECG_EMG.pdf, Dated Sep. 2, 2010.
AADE, "AADE 37th Annual Meeting San Antonio Aug. 4-7, 2010" American Association of Diabetes Educators Aug. 2010; http://www.diabeteseducator.org/annualmeeting/2010/index.html; 2 pp.
Arshak et al., A Review and Adaptation of Methods of Object Tracking to Telemetry Capsules IC-Med; Jan. 2007 vol. 1, No. 1, Issue 1, 12pp.
"ASGE Technology Status Evaluation Report: wireless capsule endoscopy" American Soc. for Gastrointestinal Endoscopy; Apr. 2006 vol. 63, No. 4; 7 pp.
Aydin et al., "Design and implementation considerations for an advanced wireless interface in miniturized integrated sensor Microsystems" Sch. of Eng. & Electron, Edinburgh Univ., UK; Sep. 2003; Abstract Only.
Bohidar et al., "Dielectric Behavior of Gelatin Solutions and Gels" Colloid Polym Sci (1998) 276:81-86.
Brock, "Smart Medicine: The Application of Auto-ID Technology to Healthcare" Auto-ID Labs (2002) http://www.autoidlabs.org/uploads/media/MIT-AUTOID-WH-010.pdf.
Coury, L. "Conductance Measurement Part 1: Theory"; Current Separations, 18:3 (1999) p. 91-96.
Delvaux et al., "Capsule endoscopy: Technique and indications" Clinical Gastoenterology; Oct. 2008 vol. 22, Issue 5, 1 pp. (Abstract Only).
Dhar et al., "Electroless nickel plated contacts on porous silicon" Appl. Phys. Lett. 68 (10) pp. 1392-1393 (1996).
Eldek A., "Design of double dipole antenna with enhanced usable bandwidth for wideband phased array applications" Progress in Electromagnetics Research PIER 59, 1-15 (2006).
Fawaz et al., "Enhanced Telemetry System using CP-QPSK Band—Pass Modulation Technique Suitable for Smart Pill Medical Application" IFIP IEEE Dubai Conference Apr. 2008; http://www.asic.fh-offenburg.de/downloads/ePille/IFIP_IEEE Dubai_Conference.pdf.
Ferguson et al., "Dialectric Constant Studies III Aqueous Gelatin Solutions" J. Chem. Phys. 2, 94 (1934) p. 94-98.
Furse C. M., "Dipole Antennas" J. Webster (ed). Wiley Encyclopedia of Electrical and Electronics Engineering (1999) p. 575-581.
Gaglani S. "Put Your Phone, or Skin, on Vibrate" MedGadget; Mar. 2012 http://medgadget.com/2012/03/put-your-phone-or-skin-on-vibrate.html 8pp.
Gilson, D.R. "Molecular dynamics simulation of dipole interactions", Department of Physics, Hull University, Dec. 2002, p. 1-43.
Given Imaging, "Agile Patency Brochure" (2006) http://www.inclino.no/documents/AgilePatencyBrochure_Global_GMB-0118-01.pdf; 4pp.
Gonzalez-Guillaumin et al., "Ingestible capsule for impedance and pH monitoring in the esophagus" IEEE Trans Biomed Eng; Dec. 2007 54(12) 1pp. (Abstract Only).
Greene, "Edible RFID microchip monitor can tell if you take your medicine" Bloomberg Businessweek; Mar. 2010 2 pp.; http://www.businessweek.com/idg/2010-03-31/edible-rfid-microchip-monitor-can-tell-if-you-take-your-medicine.html.
Halthion Medical Technologies "Providing Ambulatory Medical Devices Which Monitor, Measure and Record" webpage. Online website: http://www.halthion.com/; downloaded May 30, 2012.
Hoeksma, J. "New 'smart pill' to track adherence" E-Health-Insider May 2010 http://www.e-health-insider.com/news/5910/new_'smart_pill'_monitors_medicines.
Hoover et al., "Rx for health: Engineers design pill that signals it has been swallowed" University of Florida News; Mar. 2010 2pp.; http://news.ufl.edu/2010/03/31/antenna-pill-2/.

(56) References Cited

OTHER PUBLICATIONS

ISFET—Ion Sensitive Field-Effect Transistor; Microsens S.A. pdf document. Office Action dated Jun. 13, 2011 for U.S. Appl. No. 12/238,345; 4pp.

International Foundation for Functional Gastrointestinal Disorders—IFFGD (2012) "Diagnosis and Tests for GERD" Online article last updated Aug. 22, 2012; Downloaded Dec. 14, 2012 at http://www.aboutgerd.org/site/about-gerd/diagnosis/.

Jimbo et al., "Gastric-fluid-utilized micro battery for micro medical devices" The Sixth International Workshop on Micro and Nanotechnology for Power Geneartion and Energy Conservation Applications, (2006) pp. 97-100.

Jung, S. "Dissolvable 'Transient Electronics' Will Be Good for Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.

Juvenile Diabetes Research Foundation International (JDRF), "Artificial Pancreas Project" Jun. 2010; http://www.artificialpancreasproject.com/; 3 pp.

Kamada K., "Electrophoretic deposition assisted by soluble anode" Materials Letters 57 (2003) 2348-2351.

Lifescan, "OneTouch UltraLink™" http://www.lifescan.com/products/meters/ultralink; Jul. 2010 2 pp.

Medtronic, "CareLink Therapy Management Software for Diabetes" Jul. 2010; https://carelink.minimed.com/patient/entry.jsp?bhcp=1; 1 pp.

Medtronic, "Carelink™ USB" (2008) http://www.medtronicdiabetes.com/pdf/carelink_usb_factsheet.pdf 2pp.

Medtronic "The New MiniMed Paradigm® REAL-Time Revel™ System" Aug. 2010 http://www.medtronicdiabetes.com/products/index.html; 2 pp.

Medtronic, "Mini Med Paradigm® Revel™ Insulin Pump" Jul. 2010 http://www.medtronicdiabetes.com/products/insulinpumps/index.html; 2 pp.

Medtronic, Mini Med Paradigm™ Veo™ System: Factsheet (2010). http://www.medtronic-diabetes.com.au/downloads/Paradigm%20Veo%20Factsheet.pdf ; 4 pp.

Melanson, "Walkers swallow RFID pills for science" Engadget; Jul. 2008; http://www.engadget.com/2008/07/29/walkers-swallow-rfid-pills-for-science/.

MMS "What is Impedance?" (2012) Online article downloaded on Dec. 13, 2012 from http://www.mmsinternational.com/int/781/gastroenterology-impedance-ph-measurement-product-ohmega-video.

O'Brien et al., "The Production and Characterization of Chemically Reactive Porous Coatings of Zirconium Via Unbalanced Magnetron Sputtering" Surface and Coatings Technology (1996) 86-87; 200-206.

Owano, N., "Study proposes smart sutures with sensors for wounds" Phys.Org. Aug. 2012. http://phys.org/news/2012-08-smart-sutures-sensors-wounds.html.

Park, "Medtronic to Buy MiniMed for $3.7 Billion" (2001) HomeCare; http://homecaremag.com/mag/medical_medtronic_buy_minimed/; 2 pp.

Platt, D., "Modulation and Deviation" AE6EO, Foothills Amateur Radio Society; Oct. 26, 2007; 61 pp.

"RFID "pill" monitors marchers" RFID News; Jul. 2008 http://www.rfidnews.org/2008/07/23/rfid-pill-monitors-marchers/.

Rolison et al., "Electrically conductive oxide aerogels: new materials in electrochemistry" J. Mater. Chem. (2001) 1, 963-980.

Roulstone, et al., "Studies on Polymer Latex Films: I. A study of latex film morphology" Polymer International 24 (1991) pp. 87-94.

"SensiVida minimally invasive clinical systems" Investor Presentation Oct. 2009 28pp; http://www.sensividamedtech.com/SensiVidaGeneralOctober09.pdf.

Shin et al., "A Simple Route to Metal Nanodots and Nanoporous Metal Films"; Nano Letters, vol. 2, No. 9 (2002) pp. 933-936.

Shrivas et al., "A New Platform for Bioelectronics-Electronic Pill", Cummins College, (2010).; http://www.cumminscollege.org/downloads/electronics_and_telecommunication/Newsletters/Current%20Newsletters.pdf; First cited in third party client search conducted by Patent Eagle Search May 18, 2010.

"Smartlife awarded patent for knitted transducer" Innovation in Textiles News: http://www.innovationintextiles.com/articles/208.php; 2pp. Aug. 2009.

"The SmartPill Wireless Motility Capsule" Smartpill, The Measure of GI Health; May 2010 http://www.smartpillcorp.com/index.cfm?pagepath=Products/The_SmartPill_Capsule&id=17814.

Solanas et al., "RFID Technology for the Health Care Sector" Recent Patents on Electrical Engineering (2008) 1, 22-31.

Swedberg, "University Team Sees Ingestible RFID Tag as a Boon to Clinical Trials" RFID Journal Apr. 27, 2010; http://www.rfidjournal.com/article/view/7560/1 3pp.

U.S. Appl. No. 12/238,345, filed Sep. 25, 2008, Hooman et al., Non-Final Office Action mailed Jun. 13, 2011 22pp.

Walkey, "MOSFET Structure and Processing"; 97.398* Physical Electronics Lecture 20; Office Action dated Jun. 13, 2011 for U.S. Appl. No. 12/238,345; 24 pp.

Watson, et al., "Determination of the relationship between the pH and conductivity of gastric juice" Physiol Meas. 17 (1996) pp. 21-27.

Wongmanerod et al., "Determination of pore size distribution and surface area of thin porous silicon layers by spectroscopic ellipsometry" Applied Surface Science 172 (2001) 117-125.

"PALO Bluetooth Baseband" PALO Bluetooth Resource Center (2002) Retrieved from Internet Dec. 12, 2012 at URL: http://palowireless.com/bluearticles/baseband.asp; first cited in Office Action dated Jan. 17, 2013 for EP08853901.0.

Trutag, Technologies, Inc., Spectral Microtags for Authentication and Anti-Counterfeiting; "Product Authentication and Brand Protection Solutions"; http://www.trutags.com/; downloaded Feb. 12, 2013; 1 pp.

Baskiyar, S. "A Real-time Fault Tolerant Intra-body Network" Dept. of Comp. Sci & Soft Eng; Auburn University; Proceedings of the 27th Annual IEEE Conference; 0742-1303/02 (2002) IEEE; 6 pp.

Hotz "The Really Smart Phone" The Wall Street Journal, What They Know (2011); 6 pp.; http://online.wsj.com/article/SB10001424052748704547604576263261679848814.html?mod=djemTECH_t.

Lin et al., "Do Physiological Data Relate to Traditional Usability Indexes?" Proceedings of OZCHI 2005, Canberra, Australia (2005) 10 pp.

Mandryk et al., "A physiological approach for continuously modeling user emotion in interactive play environments" Proceedings of Measuring Behavior (2008) (Maastrichtm the Netherlandsm Aug. 26-29) 2 pp.

Mandryk et al., "Objectively Evaluating Entertainment Technology" Simon Fraser University; CHI (2004) ACM 1-58113-703-6/0410004; 2 pp.

Winter, J. et al. "The material properties of gelatin gels"; USA Ballistic Research Laboratories, Mar. (1975), p. 1-157.

* cited by examiner

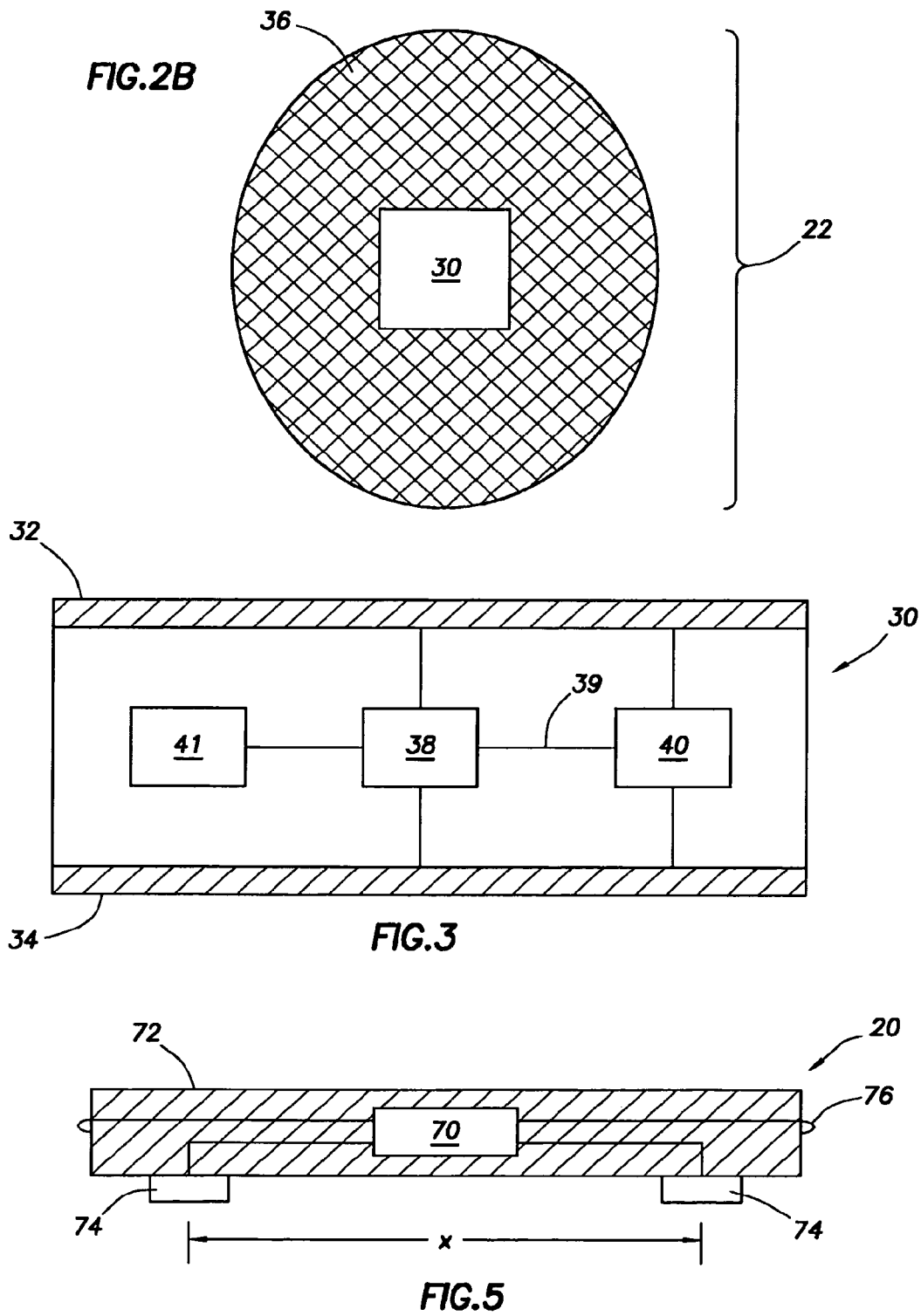

EVALUATION OF GASTROINTESTINAL FUNCTION USING PORTABLE ELECTROVISCEROGRAPHY SYSTEMS AND METHODS OF USING THE SAME

CROSS REFERENCE

Pursuant to 35 U.S.C. §119 (e), this application claims priority to the filing dates of U.S. Provisional Application Ser. Nos. 61/121,878 filed on Dec. 11, 2008, and U.S. Provisional Application Ser. Nos. 61/121,881 filed on Dec. 11, 2008, each of the disclosures of which is herein incorporated by reference in their entirety.

FIELD OF THE INVENTION

The present invention is related to electronic systems and, more specifically, to electronic systems for determining electrical signals generated by a subject.

INTRODUCTION

Gastrointestinal disorders are responsible for a variety of different medical conditions. One type of gastrointestinal disorder is gastric motility disorders. Gastric motility disorders can include gastric dysrhythmias (such as bradygastria and tachygastria), gastroparesis and gastric outlet obstruction. Gastric motility disorders may arise from multiple different causes, such as autonomic neuropathy secondary to diabetes, prior abdominal surgery, various diseases such as autoimmune disorders, drug side effects, etc. Symptoms of gastric motility disorders may vary, and may include nausea, vomiting, bloating and abdominal discomfort. The symptoms may be mild, or may develop into chronic, severe, or even debilitating conditions, which adversely affect the physical and/or mental well-being of an individual.

Another type of gastrointestinal disorder is gastroesophageal reflux disease (GERD), which is characterized by chronic symptoms or mucosal damage produced by the abnormal reflux in the esophagus. DeVault K R, Castell D O (1999). "Updated guidelines for the diagnosis and treatment of gastoesophageal reflux disease. The Practice Parameters Committee of the American College of Gastroenterology". Am. J. Gastroenterol. 94 (6): 1434-42. GERD may arise from transient or permanent changes in the barrier between the esophagus and the stomach. These changes can arise from incompetence of the lower esophageal sphincter, transient lower esophageal sphincter relaxation, impaired expulsion of gastric reflux from the esophagus, or a hiatus hernia.

A variety of different tests associated with gastrointestinal disorders exists. One type of test that has been developed for evaluating gastromotility is the Gastric Emptying Scintigraphy (GES) test. GES is considered the gold-standard diagnostic test for gastroparesis. Other tests that may be employed for gastric motility disorders include barium studies, ultrasound, CAT scan, magnetic resonance imaging (MRI), endoscopy, manometry, and electrogastrograms.

An electrogastrogram (EGG) is a graphic produced by an electrogastrograph, which records the myoelectrical signals which travel through the stomach muscles and control the contractions of the stomach muscles. An electrogastroenterogram (or gastroenterogram) is analogous to an electrogastrogram, with the exception that electric signals arising from both the stomach and the intestines are employed.

To obtain electrogastrograms and electrogastroenterograms, sensors (such as electrodes) are applied to the skin surface of a patient and employed to detect electrical signals indicative of muscular activity of the gastrointestinal system, or region of interest thereof.

The problem with systems currently being used that employ skin surface readings is that the electrical signals associated with abdominal muscular activity are hard to distinguish from electrical signals indicative of muscular activity of the gastrointestinal system. Therefore what is needed is a system and method for accurately reading and detecting electrical signals indicative of muscular activity of the gastrointestinal system.

SUMMARY

In accordance with the teaching of the present invention, systems and methods are disclosed for capturing electrical signals associated with muscular activity of the gastrointestinal system. The systems and method disclosed herein can be used with electroviscerography systems and methods of evaluating gastrointestinal function in a subject. Aspects of the system include an ingestible identifier marker and a body-associated receiver configured to detect electrical signals. The system is configured to receive data from the identifier unit or marker. The information can be used to generate an electroviscerogram from the received data. Also provided are methods of producing electroviscerograms using the markers and receivers according to the present invention.

BRIEF DESCRIPTION OF THE FIGURES

FIG. 2B is a top view of the identifier unit of FIG. 2A.

FIG. 3 is a functional component block diagram of the integrated circuit of the identifier unit of FIG. 2A.

FIG. 5 is a functional component block diagram of the receiver unit of FIG. 1.

DETAILED DESCRIPTION

Figure 1:
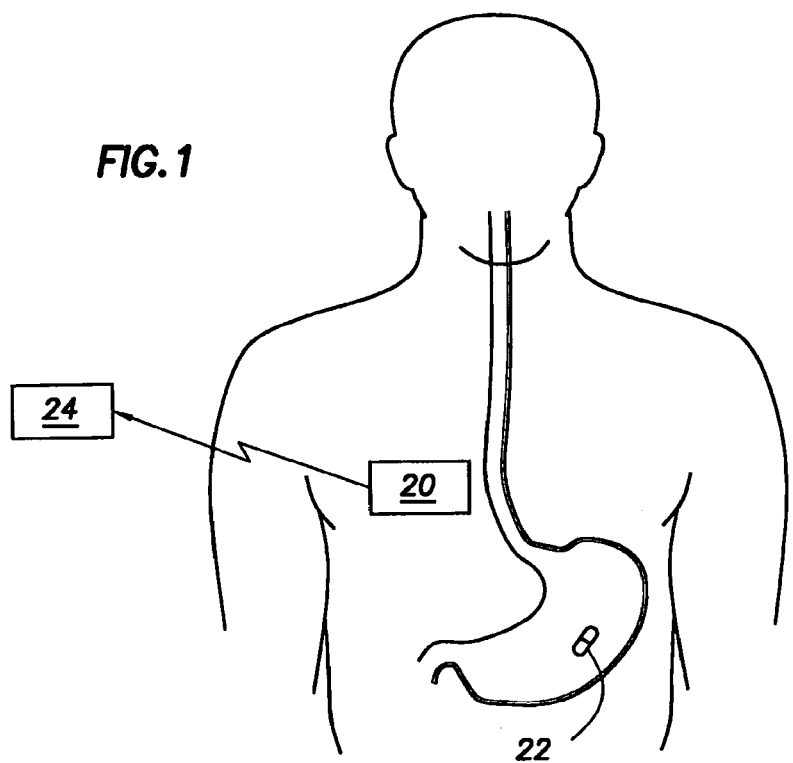
FIG. 1 is an illustrative example of a receiver unit attached to a subject and an identifier unit ingested by the subject.

Referring FIG. 1, a subject is shown with a portion of an electroviscerography system that collects data about the subject in accordance with the teaching of the present invention. The electroviscerography system includes a body-associated receiver unit 20 and an identifier unit 22. An extra-corporeal data processor 24 communicates with the receiver unit 20. The extra-corporeal data processor 24 may take a variety of configurations, such as a computer with a built-in or peripheral monitor (such as may be found in a bedside monitor or a health information system), a personal digital assistant (PDA), a smart phone, a messaging device, etc. To provide data to the extra-corporeal data processor 24, the receiver unit 20 may be configured to re-transmit data of a received signal to the location external to said subject. Alternatively, the receiver may be configured to be interrogated by an external interrogation device to provide data of a received signal to an external location. Any convenient data transmission protocol may be employed, including both wired and wireless data transmission protocols.

The electroviscerography systems of the invention are systems configured to produce electroviscerograms. Electroviscerograms refer to any usable manifestation of data, such as graphical reports that can be used to evaluate gastrointestinal function in a subject. Gastrointestinal information includes one or more parameters that provide information about the myoelectrical activity of a visceral organ or the gastrointestinal system or a portion thereof. Visceral organs of a subject are the soft internal organs of the body, especially those contained within the abdominal and thoracic cavities. Of interest are organs involved in motility, such as organs of the gastrointestinal tract. The term "gastrointestinal" relates to the stomach and intestines. The phrase "gastrointestinal system" refers collectively to the stomach, small and large intestine, as well as related structures, such as esophagus, etc. As such, electroviscerograms produced by systems of the invention include electroenterograms and electrogastrograms. Additional visceral organs of interest include organs of the urinary tract, such as the bladder, etc.

According to one aspect of the present invention, the subject ingests the identifier unit 22 in order to activate the identifier unit 22. As shown in the current example of FIG. 1, the identifier unit 22 is at an advanced ingested stage. The receiver unit 20 is shown secured to the subject at a desired location. The location of the receiver unit 20 can be determined by the medical requirements and the system design. The receiver unit 20 employed in accordance with the aspects of the present invention are those that are configured to be associated with a body location (either inside of or on a surface of a body) and to detect electrical signals from one or more visceral organs of the body, such as the gastrointestinal tract or a portion thereof, such as the stomach, small intestine, large intestine, etc. It is also within the scope of the present invention, as detailed below, to have the receiver unit 20 attached to the clothing of the subject with just electrode leads/wires secured to the skin of the subject.

Figure 2A:
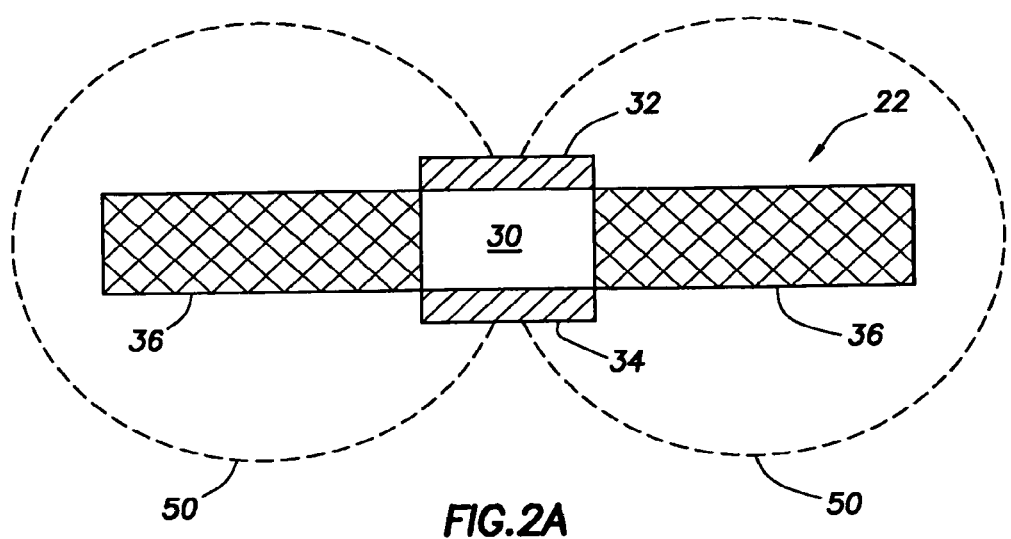
FIG. 2A is a cross-sectional side view of the identifier unit of FIG. 1 in accordance with the teachings of the present invention.

Referring now to FIGS. 2A and 2B, identifier unit 22 includes an integrated circuit component 30, an upper electrode 32, a lower electrode 34, and a signal amplification element 36. According to the teachings of the present invention, the upper and lower electrodes 32 and 34, respectively, may have any convenient shape, e.g., square, disc, etc. The signal amplification element 36 is a planar disc structure, where the edge of the signal amplification element 36 extends beyond the edge of the upper electrode 32 and the lower electrode 34. In the depicted embodiment, the radius of the signal amplification element 36 is longer than the radius of the upper electrode 32 and the lower electrode 34, e.g., by 1 mm or more, such as by 10 mm or more.

The distance that the edge of the signal amplification element 36 may extend beyond the edge of electrodes 32 and 34 may vary, and in certain embodiments is 0.05 mm or more, e.g., 0.1 mm or more, including 1.0 mm or more, such as 5.0 mm or more and including 10 mm or more, where the distance may not exceed 100 mm in certain embodiments. The upper electrode 32 and lower electrode 34 are configured such that upon contact with a conducting fluid, such as stomach fluid, a voltage potential is created and current flows through the integrated circuit 30 to cause one or more functional blocks in the integrated circuit 30 to produce a unique current signature when the identifier unit 22 is operating in the broadcast mode. The voltage potential created between the upper electrode 32 and the lower electrode 34 is created through a chemical reaction between materials that make-up the electrodes 32/34 and the surrounding conducting fluid. In the broadcast mode, current paths 50 are formed between upper electrode 32 and lower electrode 34 through the conducting fluid surrounding the identifier unit 22.

Referring now to FIG. 3, the integrated circuit 30 includes a control unit 38 electrically coupled to a detection unit 40 and a sensing unit 41. In broadcast mode, the control unit 38 of the integrated circuit 30 controls the conductance between the upper and lower electrodes 32 and 34 respectively. Through controlling the conductance, the identifier unit 22 is able to produce a unique current signature and has encoded therein data gathered by the identifier unit 22 during the detection mode. In the detection mode the detection unit 40 detects the myoelectrical activity of the visceral organs or the gastrointestinal system or a portion thereof. Myoelectric signals have frequencies ranging from a few hertz to about 300 Hz, and voltages ranging from approximately 10 microvolts to 1 millivolt. Depending on the embodiment, the target physiological site or location of activation of the identifier unit 22 may vary. Representative target physiological sites of interest include, but are not limited to: a location in the gastrointestinal tract, such as the mouth, esophagus, stomach, small intestine, large intestine, etc. Identifiers may be configured to be activated upon contact with fluid at the target site, e.g., stomach fluid, regardless of the particular composition of the target site. Where desired, the identifier may be configured to be activated by interrogation, following contact of the composition with a target physiological site. The identifier unit 22 may be configured to be activated at a target site, wherein the target site is reached after a specified period of time.

The sensing unit 41 includes circuitry for sensing and detection of various parameters associated with the environment. For example, the sensing unit 41 may be a temperature sensing or a pH sensing unit or a combination thereof. Other physiological parameter sensing sensors may be included.

Figure 4:
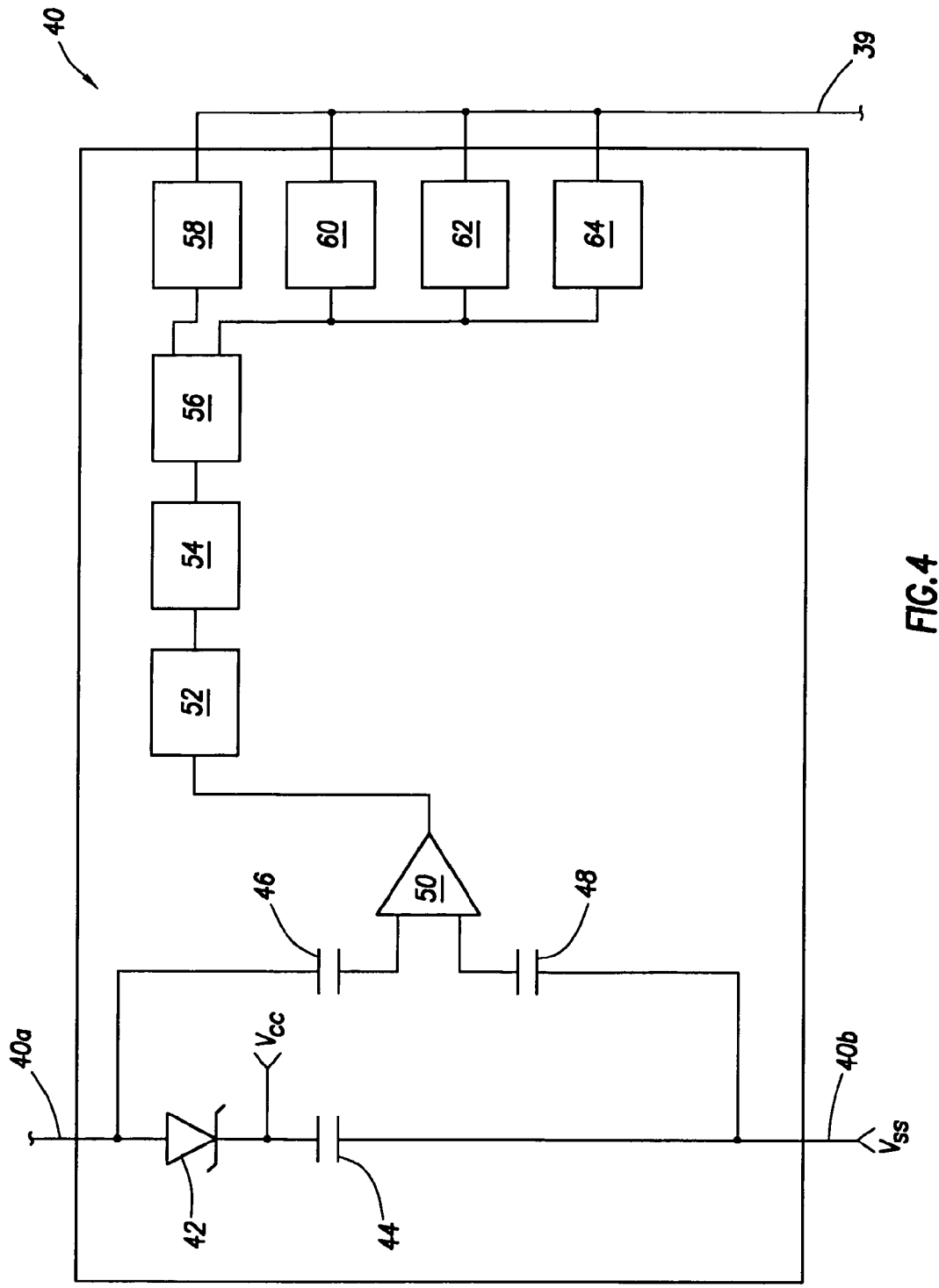
FIG. 4 is a functional component block diagram of the detection unit of the integrated circuit of FIG. 3.

Referring now to FIG. 4, the detection unit 40 includes power/signal lines 40a and 40b for powering the circuitry that detects the myoelectrical activity of the visceral organs when the identifier unit 22 is operating in detection mode. The myoelectric currents are typically lower frequency current sources. The power lines 40a and 40b are electrically coupled to a zener diode 42 and capacitor 44 for power supply control. Additionally, the power lines 40a and 40b are electrically coupled in parallel to capacitors 46 and 48 and amplifier 50 for detection and filtering of the electrical signals associated with the myoelectrical activity of the visceral organs. More specifically, the signal passes through amplifier 50. The amplified signal is passed to the bandpass filter unit 52. At the filter unit 52 removes the high frequency portion of the signals so that the myoelectrical activity and the associated signals are left. The filtered information is passed to a peak detection unit 54. The peak detection unit 54 is used to determine if a signal is associated with a true myoelectric activity as well as the proximity of the activity to the identifier unit 22, all which can be determined by the peak power or spike that occur. The peak detection unit 54 is able to adjust the reference or base-line values using the desired detection parameters. If there is a peak in voltage potential that exceeds the threshold value set by the peak detection unit 54, then the peak spike signal is passed to a pattern recognition unit 56 to determine the nature and type of myoelectric signal. The output of the pattern recognition unit 56 is received by a signal acknowledgement module 58, an IPG filter 60, a physiological parameter filter 62, and a second physiological parameter filter 64. Each filter 60, 62, and 64 are set to determine and allow only a specific type of detected electrical activity to pass through each filter's defined range. For example, if the information detected and collected by the identifier unit 22 is low frequency myoelectric current and then only one of the three filters 60, 62, and 64 will be passed the information to the connector 39. Any number of filters can be added to the detection unit 40 depending on the parameters are being evaluated. For example, one filter may be added to allow only information related pH to pass to the control unit 38. Once the information is passed through one of the filters on the detection unit 40, then the data or information is sent to the control unit 38 where it is encoded as part of the unique current signature that the control unit 38 produces. This unique current signature is detected and decoded by the receiver units of the system.

According to some aspects of the present invention, the identifier unit 22 is physiologically sized, by which is meant that it, alone or in combination with other vehicles, is compatible with ingestion. In certain aspects, the identifier unit may be associated with a carrier such as an active pharmaceutical agent or other vehicle. For example, physiologic sized identifier units may have a size of 10 mm$^3$ or smaller, such as 5 mm$^3$ or smaller, including 1 mm$^3$ or smaller. In other instances, the identifier unit 22 may be sized to remain in the stomach following ingestion, at least until the identifier unit 22 is broken up by the digestive action of the stomach. In these instances, the identifier unit 22 may be configured to have a surface area of 1 cm$^2$ or greater, such as 10 cm$^2$ or greater.

The receiver unit 20 and the identifier unit 22 are configured to detect electrical or magnetic field signals. The processor 24 can be used or configured to receive data from receiver unit 20 via any communication means, including wireless and wired methods. The processor 24 can generate an electroviscerogram from the received data. The receiver unit 20 of interest includes those that are sized to be stably associated with a living subject in a manner that does not substantially impact movement of the living subject. As such, the receiver unit 20 may have dimensions that, when employed with a subject, such as a human subject, will not cause the subject to experience any difference in its ability to move. In some instances, the receiver unit 20 is dimensioned such that its size does not hinder the ability of the subject to physically move. Where desired, the receiver unit 20 has a small size and may occupy a volume of space of 5 cm$^3$ or less, such as 3 cm$^3$ or less, including 1 cm$^3$ or less. In some instances, the receiver has a chip size limit ranging from 10 mm$^2$ to 2 cm$^2$.

Referring now to FIG. 5, the receiver unit 20 includes a processing unit 70 positioned in a housing 72. The processing unit 70 is electrically coupled to and connected to electrodes 74. A coil 76 is wrapped around the hosing 72 and electrically coupled to the processing unit 70. The coil 76 is wound around the perimeter and provides for signal transmission from the receiver unit 20 device to an extra-corporeal data processor 24 of FIG. 1. In the current example, the receiver unit 20 includes two electrodes. However, in accordance with another aspect of the present invention, the receiver unit 20 may include additional electrodes and the scope of the present invention is not limited by the number electrodes. Thus, in one configuration of interest, the receiver unit 20 includes one or more electrodes (such as two or more electrodes, three or more electrodes, and/or includes multiple, such as two or more, three or more, four or more pairs of electrodes, etc.) for detecting electrical signals emitted by the visceral organ of interest as well as detection of the current signature from the identifier unit 22. In one configuration of interest, the receiver unit 20 includes two electrodes that are dispersed at a distance "X" from each other, which distance may be one that allows the electrodes to detect a differential voltage. This distance may vary, and may range from 0.1 to 5 cm, such as from 0.5 to 2.5 cm. The electrodes may also serve as an antenna to receive a signature current associated with an identifier unit or marker.

The receiver unit 20 may include a variety of different types of signal receiver elements and processing protocols, as long as the receiver unit 20 is configured to detect the desired visceral electrical signals. Additionally, the receiver unit of interest may be both external and implantable.

Figure 6:
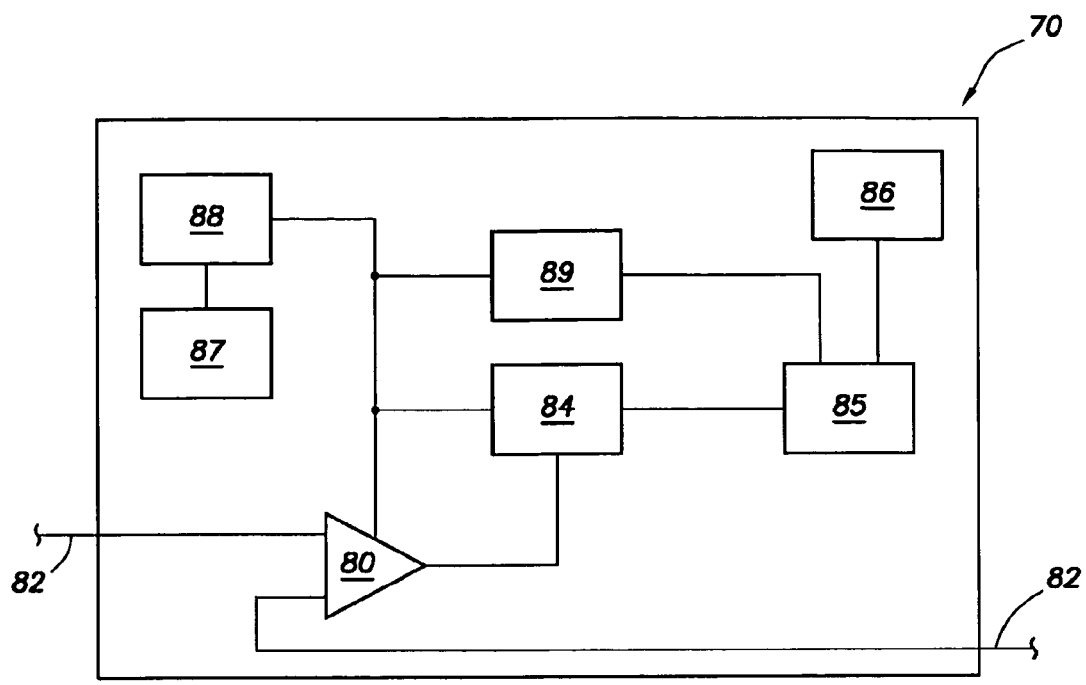
FIG. 6 is a block diagram representation of the receiver unit of FIG. 1.

Referring now to FIG. 6, the processing unit 70 includes an amplifier 80 that detects the differential voltage potential across the electrodes 74 of FIG. 5. This voltage potential difference represents the myoelectric signal across the electrodes. The potential is sent to the amplifier 80 through leads 82 that are electrically connected to the electrodes 74 of FIG. 5 via the amplifier. The detected signal then goes into the demodulator 84. Also shown is a memory unit 85 to store the demodulated data, received signal, physiological parameter data, as well as medical record data. A clock 86 writes to the memory unit 85 in order to time-stamp the events. A transmit unit 89 transfers data from the memory unit 85 to the extra-corporeal data processor unit 24 of FIG. 1. The processing unit 70 also includes a power source 87 electrically coupled to a microprocessor 88. The microprocessor 88 coordinates the function between the various functional blocks as well as power management.

According to various aspects of the present invention, the system of the invention may include a single receiver unit or multiple receiver units. For systems that include a single receiver unit, the receiver unit may include three or more distinct electrodes, and may be configured to be positioned in an abdominal or xyphoid region of the subject. The receiver unit of such systems may be positioned at any convenient location, such as the front of a torso, the back of a torso, etc., as desired. In systems that have multiple receiver units, each receiver may have a single electrode and such receivers may be in communication with one another to create an array of receiver units.

Aspects of implantable versions of the receiver unit will have a biologically compatible enclosure, one or more sense electrodes, a power source, which could either be a primary cell or rechargeable battery, or one that is powered by broadcasting inductively to a coil. For the external signal receivers, embodiments include structures that have electrodes opposed to the skin. The communication may be wireless or performed over one or more conductive media, e.g., wires, optical fibers, etc. Where desired, the same electrodes may be used for receiving and transmitting signals.

In certain embodiments, the components or functional blocks of the present receivers are present on integrated circuits, where the integrated circuits include a number of distinct functional blocks, i.e., modules. Within a given receiver, at least some of, e.g., two or more, up to an including all of, the functional blocks may be present in a single integrated circuit in the receiver. By single integrated circuit is meant a single circuit structure that includes all of the different functional blocks. As such, the integrated circuit is a monolithic integrated circuit that is a miniaturized electronic circuit (which may include semiconductor devices, as well as passive components) that has been manufactured in the surface of a thin substrate of semiconductor material. The integrated circuits of certain embodiments of the present invention may be hybrid integrated circuits, which are miniaturized electronic circuits constructed of individual semiconductor devices, as well as passive components, bonded to a substrate or circuit board.

Signal receivers of interest include, but are not limited to, those receivers disclosed in: PCT application serial no. PCT/US2006/016370 published as WO 2006/116718; PCT application serial No. PCT/2007/24225 published as WO 2008/063626; PCT application serial no. PCT/US2008/52845 published as WO/2008/095183; the disclosures of which applications are herein incorporated by reference.

In accordance with other aspects of the present invention, the system may include two or more (such as three or more, including four or more) receiver units. In such systems, the two or more body-associated receivers may be adaptively arranged at any desired location on the body of the subject. For example, all of the body-associated signal receivers may be present on the same side of a body, such as the front torso of a body, or they may be present on opposite sides of a body, such as the front and back of the torso of a body.

In addition to the one or more body-associated signal receivers, systems of the invention may include an extra-corporeal data processor configured to receive data from the body-associated receiver and generate an electroviscerogram from the received data. The extra-corporeal data processor unit 24 may receive the electrical signal data directly from the receiver unit, or via a data relay device (such as a device that receives data from the receiver unit and then forwards the received data to an extra-corporeal data processor). The extra-corporeal data processor unit 24 may be configured to receive the data via any convenient wired or wireless protocol, as desired. Extra-corporeal data processors of interest are those that can receive the electrical signal data and process the data to produce an electroviscerogram. The produced electroviscerograms may be output to a user by any convenient medium, such as writing the electroviscerograms on paper, displaying an electroviscerogram to a user via a graphical user interface, and the like. Extra-corporeal data processors of the systems of the invention may take a variety of configurations, such as a computer with a built-in or peripheral monitor (for example as embodied in a bedside monitor or a health information system), a personal digital assistant (PDA), a smart phone, a messaging device, etc.

In some instances, the identifier unit identifier is environmentally sensitive. By environmentally sensitive is meant that the identifier is configured to be activated when the identifier comes into contact with one or more conditions to which the identifier is designed to respond. Environmental conditions to which identifiers of interest may be configured to respond include temperature, pressure, pH, analyte presence, etc. In some instances, the identifiers are pH sensitive, by which is meant that the identifiers are configured to respond to predetermined pH conditions, such as acidic or alkaline conditions. For example, an identifier may be configured to respond (for example by activation and emission of a signal) when it contacts fluid having an acidic pH (such as pH 6.5 or less, such as pH 6 or less) or fluid having an alkaline pH (such as pH of 7.5 or higher, such as pH of 8 or higher). As environmentally sensitive identifiers are responsive to a predetermined condition or set of two or more conditions to which they are exposed, they are configured to activate and emit a signal upon contact with the predetermined condition or set of conditions.

Depending on the needs of a particular application, the current detected by the receiver unit from the identifier unit may be generic, such that it merely identifies that the identifier has contacted the target site. Alternatively, the signal may be represent information about the myoelectric activity as detected by the identifier unit. As such, the identifier may be one that, when employed with a batch of dosages, emits a signal which cannot be distinguished from the signal emitted by the identifier of any other dosage member of the batch. Alternatively, each member of the batch may have an identifier that emits a unique signal, at least with respect to all the other identifiers of the members of the batch. In these instances, each identifier of the batch emits a signal that uniquely identifies that particular identifier in the batch, at least relative to all the other identifiers of the batch. The identifier may emit a unique signal that is a universally unique signal (where such a signal may be analogous to a human fingerprint which is distinct from any other fingerprint of any other individual and therefore uniquely identifies an individual on a universal level). The signal may either directly convey information about a given event, or provide an identifying code, which may be used to retrieve information about the event from a database (for example a database linking identifying codes with compositions).

The identifier may generate a variety of different types of signals, including but not limited to: current signatures produced through controlling conductance, RF signals, magnetic signals, conductive (near field) signals, acoustic signals, etc. The transmission time of the identifier may vary, where in certain instances the transmission time may range from 0.1 μsec to 48 hours or longer, such as from 0.1 μsec to 24 hours or longer, such as from 0.1 μsec to 4 hours or longer, such as from 1 sec to 4 hours, including from 1 minute to 10 minutes. Depending on the given embodiment, the identifier may produce a unique current signature once. Alternatively, the identifier may be configured to produce a unique current signature with the same information (identical signals), two or more times, where the collection of discrete identical signals may be collectively referred to as a redundant signal.

In some instances, the identifier marker may be configured to remain at a location of the gastrointestinal tract once it reaches that location. For example, the marker may include a muco-adhesive element that, upon contact with an internal location of the gastrointestinal tract, will cause the marker to remain at that location. An example of use of such an embodiment is where multiple identifier units that include a muco-adhesive element are administered to a subject. The markers will adhere to different positions of the stomach and will emit signals from different locations. The multiple different signals may be employed to produce a map of the stomach, which may be monitored over time. Where desired, the map may be monitored in response to different states, such as mealtimes, fasting, etc.

The identifiers may vary depending on the particular embodiment and intended application of the composition so long as they are activated (i.e., turned on) upon contact with a target physiological location, such as the stomach. Identifier may include an activation component, such as a battery that is completed by stomach acid, and a transmission element. Examples of different types of identifiers of interest include; but are not limited to, those identifiers described in PCT application serial no. PCT/US2006/016370 published as WO/2006/116718; PCT application serial no. PCT/US2007/082563 published as WO/2008/052136; PCT application serial no. PCT/US2007/024225 published as WO/2008/063626; PCT application serial no. PCT/US2007/022257 published as WO/2008/066617; PCT application serial no. PCT/US2008/052845 published as WO/2008/095183; PCT application serial no. PCT/US2008/053999 published as WO/2008/101107; PCT application serial no. PCT/US2008/056296 published as WO/2008/112577; PCT application serial no. PCT/US2008/056299 published as WO/2008/112578; and PCT application serial no. PCT/US2008/

077753; and U.S. patent application Ser. No. 12/564,017 filed on Sep. 21, 2009, the disclosures of which are herein incorporated by reference.

In addition to the identifier component described above, the identifier units employed in methods of the invention may be associated with a vehicle component. Vehicle components may include one or more constituents, including but not limited to fillers, binders, disintegrants, coloring agents, etc. Vehicle components of interest are further reviewed in PCT Application Serial No. US2006/016370 published as WO 2006/116718, the disclosure of which is herein incorporated by reference. Additional disclosure of components that can be present in compositions of the invention can be found in Remington's Pharmaceutical Sciences, Mace Publishing Company, Philadelphia, Pa., 17th ed. (1985). The identifier unit may be configured in a variety of different formats. Formats of interest include solid formats, such as tablets, powders, coated granules, filled capsules, etc.

Depending on the particular method, the identifier unit may not include a pharmaceutically active agent. As such, the identifier and any vehicle component or components that make up the identifier unit do not include an active agent. In yet other embodiments, the identifier unit includes an active agent. As used herein, the term "active agent" includes any compound that produces a physiological result, for example a beneficial or useful result, upon contact with a living organism, such as a human. Active agents are distinguishable from vehicle components such as fillers, binders, coloring agents, etc. The active agent may be any molecule that is capable of modulating a biological process in a living subject. In some instances, the active agent may be a substance used in the diagnosis, treatment, or prevention of a disease or as a component of a medication. Broad categories of active agents of interest include, but are not limited to: cardiovascular agents; pain-relief agents, e.g., analgesics, anesthetics, anti-inflammatory agents, etc.; nerve-acting agents; chemotherapeutic (such as anti-neoplastic) agents; etc. Active agents of interest are further disclosed in PCT Application Serial No. US2006/016370 published as WO 2006/116718, the disclosure of which is herein incorporated by reference.

A given identifier unit may include a single identifier, or two or more identifiers. The identifiers may be arranged in a variety of different configurations with respect to the other components of the marker. Where the marker includes a tablet as a vehicle, the identifier or identifiers may be arranged on a surface of the tablet vehicle. In some instances, the marker is made up of two or more identifiers present in an ingestible container. For example, multiple identifier unit identifiers may be present in a capsule fabricated from a material that dissolves upon contact with stomach fluid. Materials of interest from which the carrier components may be fabricated include physiologically acceptable polymeric materials that are used in conventional pharmaceutical capsule dosages. The materials may be clear or opaque, and may be colored as desired. Of interest are both rigid and elastic materials. Suitable polymers from which carrier components of the invention may be fabricated include, but are not limited to: polyvinyl alcohol (PVA); natural and synthetic polysaccharides, including pullulan, carrageenan, xanthan, chitosan agar gums, and cellulosic materials, such as carboxymethylcellulose, hydroxypropylmethylcellulose (HPMC), methylcellulose, hydroxyethylcellulose, hydroxyethyl methylcellulose, hydroxypropylcellulose; polyethylene glycols (PEGs), polyethylene oxides (PEOs), mixtures of PEGs and PEOs; acrylic and methacrylic acid based polymers, such as EUDRAGIT E™, EUDRAGIT L™ and/or EUDRAGIT S™ methacrylic acid polymers), EUDRAGIT RL™ and/or EUDRAGIT RS™ ammonium methacrylate copolymers; povidone (polyvinyl pyrrolidone), polyglycolysed glycerides (such as GELUCIRE 44/14™, GELUCIRE 50/02™, GELUCIRE 50/13™ and GELUCIRE 53/10™ polymers); carboxyvinyl polymers (such as CARBOPOL™ polymers); polyoxyethylene-polyoxypropylene copolymers (such as POLOXAMER188™ polymer); and the like. The capsule components may be fabricated using any convenient protocol, including molding, etc. Fabrication protocols of interest include, but are not limited to, those described in U.S. Pat. Nos. 5,705,189; 4,576,284; 4,591,475; 4,655,840; 4,738,724; 4,738,817 and 4,790,881; the disclosures of which are herein incorporated by reference. Alternatively, the capsule component may be obtained from a commercial vendor, such as Qualicaps Inc., Whitsett N.C.

Methods of producing an electroviscerogram for a subject are also provided. As reviewed above, an electroviscerogram is any usable manifestation of data, such as a graphical report (which may be written onto a physical medium or displayed on a monitor, etc.), that provides information about the myoelectrical activity of a visceral organ or organs of a subject. Visceral organs of interest include organs involved in motility, such as organs of the gastrointestinal tract, for example the stomach and intestines. As such, electroviscerograms produced by systems of the invention include electroenterograms and electrogastrograms. Additional visceral organs of interest include organs of the urinary tract, such as the bladder, etc.

In practicing methods of the invention, electrical signals generated by the visceral organ of interest (for example myoelectric signals), such as the stomach or intestine, are detected with the one or more body-associated signal receivers of the system, as described above. The resultant detected electrical signal data are then forwarded to the extra-corporeal data processor, which receives the data and generates the desired electroviscerogram from the received data. A given method may include detecting electrical signals for a given period of time, such as one hour or longer, two hours or longer, twelve hours or longer, one day or longer, two days or longer, one week or longer, two weeks or longer, one month longer, six months or longer, including one year or longer. As the systems of the invention are portable, the data may be detected and recorded continuously over these periods of time, as desired.

Depending on the particular application, the body-associated signal receiver may be positioned in a variety of different configurations relative to the organ of interest. For example, where a single body-associated signal receiver is employed, the methods may include initially positioning or implanting the single receiver at a location proximal to the organ of interest. Where the organ of interest is the stomach, the single receiver may be positioned at an abdominal or xyphoid region, as desired. With other systems that include two or more signal receivers, the receivers may be positioned at a variety of body locations. For example, the methods may include positioning two or more distinct receivers at distinct abdominal locations (for example to provide for triangulate location capability of an identifier unit as it passes through the gastrointestinal tract), or positioning one receiver at a front abdominal location and a second receiver at a back location. This latter configuration is representative of instances where the receivers are placed on opposite sides of a target organ, e.g., to measure impedance through the organ. Measuring impedance through the stomach finds interest as an independent way to evaluate gastric motility, which may be used in combination with electroviscerograms of the invention or independently thereof. For example, the measured impedance through the stomach will change depending on whether the stomach is full or empty. By correlating impedance with time following food intake, a measure of gastric motility can be readily produced.

In some instances, the identifier unit identifier is environmentally sensitive. By environmentally sensitive is meant that the identifier is configured to be activated when the identifier comes into contact with one or more conditions to which the identifier is designed to respond. Environmental conditions to which identifiers of interest may be configured to respond include temperature, pressure, pH, analyte presence, etc. In some instances, the identifiers are pH sensitive, by which is meant that the identifiers are configured to respond to predetermined pH conditions, such as acidic or alkaline conditions. For example, an identifier may be configured to respond (for example by activation and emission of a signal) when it contacts fluid having an acidic pH (such as pH 6.5 or less, such as pH 6 or less) or fluid having an alkaline pH (such as pH of 7.5 or higher, such as pH of 8 or higher). As environmentally sensitive identifiers are responsive to a predetermined condition or set of two or more conditions to which they are exposed, they are configured to activate and emit a signal upon contact with the predetermined condition or set of conditions.

For pH sensitive identifier units of the invention, pH sensitivity may be imparted to the markers using a number of different approaches. For example, the markers may include a pH sensor element, which element is configured to detect the pH of a given environment in which the marker may be placed and activate the identifier in response thereto. One example of an identifier having an integrated pH sensor is an identifier that includes an integrated circuit and three disparate electrode elements, two of which act as part of the partial power source and part of the broadcast mode while the third is used in operation during the detection mode components of the battery which is produced upon contact of the identifier with a conductive medium and the third of which (e.g., fabricated from platinum or other suitable material) serves as a counter electrode for each of the battery electrodes. The integrated circuit further includes a bandgap reference. During operation, when the identifier contacts a suitable conductive medium, such as stomach fluid, the battery electrodes provide operating voltage for the integrated circuit, including the clock component of the integrated circuit. The identifier emits a signal or signals representing temperature from the bandgap reference on the circuit and battery electrode voltages. Also transmitted from the identifier is a signal or signals providing the voltage on the reference electrode with respect to each battery electrode (for example battery electrode 1 v. Pt reference electrode and battery electrode 2 v. Pt reference electrode), where these voltages are related to pH of the environment and temperature. These signals may be transmitted as a digital signal or a frequency or a duty cycle. With such an identifier, the transmitted signal or signals are then processed, e.g., by a body-associated receiver and/or an extra-corporeal data processor, to covert the signals representing temperature and battery/reference electrode voltages into pH values, e.g., by using lookup tables or appropriate algorithms. Another approach that may be employed to impart pH sensitivity to a given marker is to include a pH sensitive coating covering activation components (such as battery elements) of the identifier, where the pH sensitive coating only dissolves to expose the activation components when the desired pH conditions are present. pH sensitive coatings of interest include, but are not limited to: cellulose acetate pthalate, EUDRAGIT L™, EUDRAGIT S™, EUDRAGIT FS™, and other pthalate salts of cellulose derivatives. Additional marker configurations that can be employed to obtained environmental sensitivity include, but are not limited to, configurations described in PCT application serial no. PCT/US2007/082563 published as WO 2008/052136, the disclosure of which is herein incorporated by reference.

In some instances, pH sensitivity is provided by an identifier unit that emits a different signal depending on the particular pH of the environment to which it is exposed. For example, an identifier may include three electrodes, one of which is coated with a pH sensitive coating which only dissolves to expose the electrode at a certain pH. In this type of identifier, a first signal will be transmitted by the uncoated electrodes and a second signal distinguishable from the first will be transmitted by the electrodes when the coating on the coated electrode is removed, e.g., by dissolution. In yet another example, the identifier may include a chemical agent that is released upon exposure to a particular pH, for example by include the agent in a chamber that is sealed with a pH sensitive coating. Upon removal of the pH sensitive coating, the agent is released and modifies the identifier emitted signal.

Yet another way to provide pH sensitivity to an identifier is to provide an element, such as a trip wire, whose conductivity is modified depending on the pH of the environment of the identifier. For example, an identifier may include a conductive trace or wire that dissolves when the identifier is exposed to a certain pH. The pH sensitivity of this element may be provided by material (for example, Mg, Zn or other metal that dissolves in acidic conditions) of the element and/or a suitable coating. When the element is present, a first signal is emitted by the identifier and when the element dissolves or is otherwise compromised, a second signal is emitted by the identifier. Alternatively, an identifier may include a conductive trace or wire that is produced when the identifier is exposed to a certain pH. For example, a trace of CuCl will convert to Cu metal upon exposure to acidic conditions to produce a conductive element. Again, the material may be covered by an appropriate coating which imparts pH sensitivity to the identifier. When the conductive element is not present, a first signal is emitted by the identifier and when the element is produced, a second signal is emitted by the identifier.

A given method may include administering a single identifier unit to a subject, or two or more identifier units, such as first, second and even third or more identifier units. As such, a given method may include administration of a single identifier unit. Alternatively, a given method may include administration of two or more, such as three or more, four or more, five or more, ten or more, fifteen or more, twenty or more, etc., identifier units to a subject. Where multiple identifier units are employed in a given method, they may be administered to a subject at the same time or at different times.

As indicated above, identifier units employed may be environmentally sensitive. In some instances where two or more environmentally sensitive identifier units are employed, the identifier units may be responsive to different environmental conditions. As such, a given method may include administering to a subject a first environmentally sensitive marker that is responsive to a first environmental condition (such as acidic conditions) and a second environmentally sensitive marker that is response to a second environmental condition (such as alkaline conditions). In such instances, the markers may be sensitive to a variety of different types of environmental conditions, such as pH.

Administration of markers may be coordinated with administration of liquid and/or foods, as desired. For example, subjects may be instructed to ingest the markers with food, including specific types of foods or meals, with liquids or during fasting, at different times of the day, etc., as desired, to obtain information that is coupled with other types of relevant information, such as caloric intake, time of day, etc.

Following administration of the one or more identifier units to a subject, as reviewed above, one or more signals emitted from the one or more identifier units are detected by a body-associated receiver of the system. The current detection is carried out through the skin and other body tissues of the subject. In some instances, the receiver is configured to simultaneously detect multiple unique current signatures each from a respective identifier unit, such as an ingestible event marker or an ionic emission module. The number of different unique current signatures from the respective number of identifier units may be 2 or more, 5 or more, 10 or more that may be emitted from different identifier units.

To provide data to the extra-corporeal data processor, the signal receiver may be configured to retransmit data of a received signal to the location external to said subject. Alternatively, the signal receiver may be configured to be interrogated by an external interrogation device to provide data of a received signal to an external location. The particular protocol employed in this evaluation may vary depending on the particular function being determined. In some instances, the evaluation protocol is one that is based on detection of a signal that is indicative of the identifier unit coming into a contact with a predetermined environmental condition of interest. For example, an evaluation protocol may be one that is based on detection of a particular pH at a particular physiological location, such as a low pH in the stomach or esophagus, which may be used in determining the presence of GERD (as reviewed in greater detail below). In these types of evaluation protocols, a single identifier unit may be employed, or multiple identifier units may be employed. For example, a set of two or more identifier units that emit differently coded signals may be employed, where the two markers are configured to emit signals at different locations.

Alternatively, each identifier unit may be configured to emit its signal at a different physiological target site, e.g., where each identifier unit is configured to be activated at a different target physiological site. For example, a first identifier unit may be activated in the mouth, a second identifier unit may be activated in the esophagus, a third identifier unit may be activated in the small intestine and a fourth identifier unit may be activated in the large intestine. Such an identifier unit set may be employed in a diagnostic application to determine function of the digestive system, such as motility through the digestive tract, gastric emptying, and the like. For example, by noting when each identifier unit emits its respective signal, a plot of signal vs. time may be generated from which information regarding digestive tract functioning may be obtained.

Instead of using a signal indicative of contact of the identifier unit with a predetermined environmental condition (such as a pH value), the evaluation protocol that is employed may monitor detected signal relative to time and location following administration. Such information may be employed to determine various aspects of gastrointestinal function, such as total GI transit time or transit times specific for portions of the gastrointestinal tract, such as gastric emptying times, small bowel transit time, total colonic transit time, and the like.

A given evaluation protocol may be one that employs data obtained solely from identifier unit 22, or may be one that employs data obtained from identifier units and one or more other types of data, such as physiologic data (including but not limited to electrogastrogram, temperature, heart rate, blood pressure, etc.), non-physiologic patient specific data (including, but not limited to gender, age, height, weight, medication history, feeding history, exercise history, etc.), environmental data (including but not limited air temperature, pressure, etc.), and the signals obtained from the body-associated signal receivers configured to obtain an electroviscerogram, such as an electroenterogram, including an electrogastrogram. The particular protocol employed to obtain the electroviscerogram may vary. For example, the particular protocol may solely employ data representing electrical signals generated by the organ of interest, i.e., organ specific myoelectric data. Alternatively, the particular protocol may employ organ specific myoelectric data and additional types of data, as reviewed above. A given protocol may include comparing data with reference, i.e., control, data to identify deviations from a norm. Another approach would be to combine data relevant to a pH with data that is relevant to myoelectric activity thereby providing the physician with powerful tools for diagnostics and decision making. A given protocol may include use of noise cancellation algorithms, as desired.

Where identifier units are employed, a given protocol may employ the signal of the identifier unit in a number of different ways, as desired. For example, the signal emitted by the identifier unit may be employed as an independent calibration of the obtained electroviscerogram. In some instances, the system employed in a given method uses an identifier unit configured to emit a signal that varies in frequency with respect to time from administration and activation. In these embodiments, changes in frequency of signal emitted by the identifier unit may be designed to reinforce or cancel out an organ of interest's myoelectric signals, such as stomach waves. For example, an identifier unit may be configured to emit signals that vary from high to low frequency as it traverses the gastrointestinal tract. Data obtained from the body-associated receiver may then be used to generate a map of both high and low frequency signals. The high frequency signals may be employed as a map of the location of the identifier unit with respect to time as it transits the gastrointestinal tract, while the low frequency signals can be employed in generating the electrogastrogram, with only those signals that resonate with the organ's myoelectric waves being employed so as to enhance the signal to noise ratio.

As discussed above with respect to FIG. 3, in yet other systems according to another aspect of the present invention, the identifier unit may itself record myoelectric signals of interest, and transmit data that includes information about these myoelectric signals to the body-associated receiver or receivers of the system. For example, the identifier unit can be configured to include a functional block which detects the myoelectric signals of interest and then transmits resultant detected myoelectric data to the one or more body-associated receiver units of the system.

A given method may include generating a clinically diagnostic score as desired, where the score may take the form of a single value or be more detailed with respect to values for one or more parameters of interest (for example, where the score is provided in the form of a report card). Using appropriate algorithms, the electroviscerograms of the invention may be combined with one or more additional data streams in order to provide this score. The methods of the invention may be employed with a variety of different types of subjects.

Figure 7:
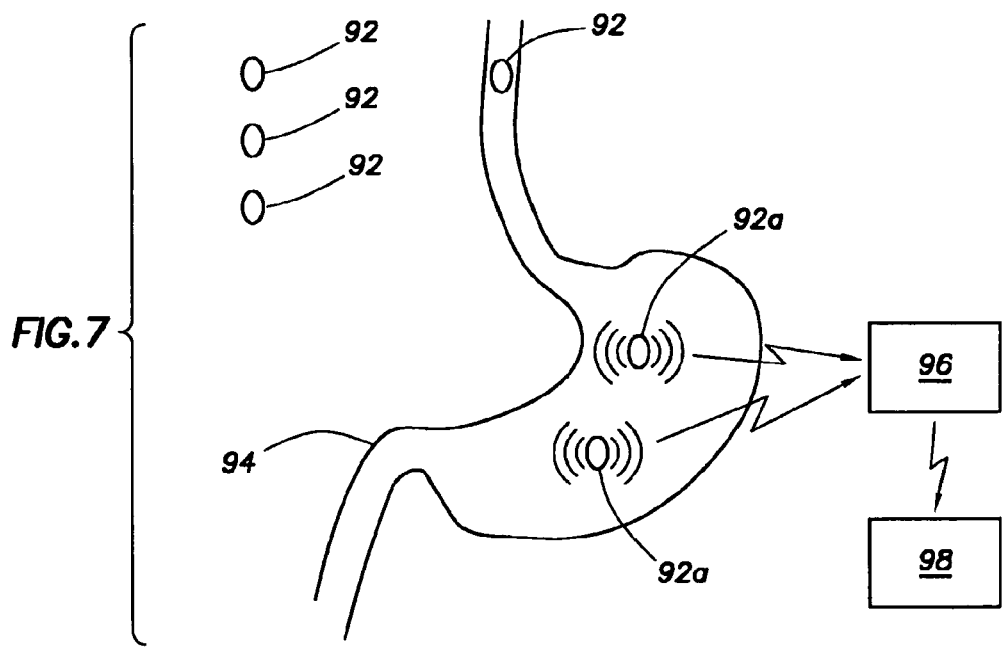
FIG. 7 shows a system for creating an array of identifier units using a receiver to coordinate position.

Referring now to FIG. 7, a schematic of a method which is employed to determine gastrointestinal transit time in a patient or subject is shown. The patient is provided three different identifier unit capsules 92, one to be taken in the morning, one to be taken in the afternoon and one to be taken in the evening. Each capsule 92 includes a set of multiple distinct identifier units that are configured to emit a signal when they reach a different portion of the gastrointestinal tract 94, such as the set of markers described above. Following administration, each capsule 92 dissolves in the stomach of the gastrointestinal tract 94 and becomes activated as active capsule 92a, each of which produces a unique current signature. The identifier unit emits a current signature as it reaches its predetermined location. The information encoded in the current signal is recorded by a receiver unit 96. The receiver unit 96 then wirelessly forwards the data to an extracorporeal data processor 98, such as a PDA or a laptop computer. The processor 98 performs an evaluation protocol on the received data to output transit time results (such as total transit time, colonic transit time, etc.) to a user (for example by displaying a graphical user interface on a monitor). The graph shown to the user via the PDA or laptop computer is a graph showing the percent emptying of the stomach as a function of time.

The methods of the invention may be employed with a variety of different types of subjects, including "mammals," carnivores (such as dogs and cats), rodentia (such as mice, guinea pigs and rats), and primates (such as humans, chimpanzees and monkeys).

The methods and systems of the invention find use in a variety of different applications in which generation of an electroviscerogram, such as an electroenterogram, like an electrogastrogram, is desired. Applications of interest include those in which electroenterograms of the invention are employed to evaluate gastrointestinal function. For example, electrogastrograms of the invention find use in the determination of stomach motility, gastric cycles, gastrointestinal transit times, stomach volume, etc. Applications of interest include use of electroviscerograms of the invention in the diagnosis and/or monitoring of gastrointestinal conditions in a subject. Gastrointestinal disorders that may be assessed in a subject using electrogastrograms of the invention include, but are not limited to: gastric motility conditions, such as gastroparesis. One application of interest is the assessment of a gastric motility condition in a subject, where assessment includes both diagnosis of the presence of a gastric motility condition in a subject as well as monitoring the progress of treatment of a subject for a gastric motility condition (for example to determine whether a given treatment protocol is having a desired therapeutic affect on the gastric motility condition of interest).

One gastric motility condition whose assessment may be achieved using methods of the invention is gastroparesis. Gastroparesis, also known as delayed gastric emptying, is a medical condition consisting of a partial paralysis of the stomach, resulting in food remaining in the stomach for a longer period of time than normal. Gastroparesis may occur when the vagus nerve is damaged and the muscles of the stomach and intestines do not work normally. Food then moves slowly or stops moving through the digestive tract. Symptoms associated with gastroparesis include vomiting, bloating, abdominal pain or discomfort and early satiety.

Subjects of interest include those at least suspected of suffering from gastroparesis, such as through the use of one or more symptoms of gastroparesis. In assessing gastroparesis in an individual, an identifier unit emits a controlled current signature as it is activated. As the identifier unit enters the gastrointestinal tract, a receiver unit's movement and position may be monitored as a function of time. For example, by plotting location as a function of time, one can readily determine when the identifier unit passes from the stomach into the small intestine after ingestion of the identifier unit, and thereby make a determination of gastric emptying time. Alternatively, a set of two or more identifier units may be employed, which markers are responsive to different environmental conditions. For example, one may administer a first identifier unit that is responsive to acidic conditions and a second identifier unit that is responsive to alkaline conditions. If these markers are administered at the same time and then the signal detection time of each is recorded, a measure of gastric emptying time can readily be made by comparing when the signals from the acidic pH and alkaline pH responsive markers are obtained. For example, the time from administration to detection of the signal from the acidic pH responsive marker may be subtracted from the time from administration to detection of the signal from the alkaline pH responsive marker in order to obtain a measure of gastric emptying time. Where desired, plots of a given parameter (such as location, pH, pressure, etc.) as a function of time may be prepared and compared to a suitable control plot (in other words reference) to obtain the desired measure of gastric emptying.

Methods of evaluating gastroparesis that may be readily modified to employ identifier units as described in the present application include, but are not limited to, those described in United States Published Application Nos. 20080287833; 20080161643; 20080064938 and 20040162501; as well as U.S. Pat. Nos. 7,160,258 and 7,141,016; the disclosures of which applications are herein incorporated by reference.

Where desired, methods of invention may be employed in conjunction with one or more additional methods of diagnosing gastroparesis. For example, methods of invention may be employed as a first determination or screen of whether or not a subject suffers from gastroparesis. If the results of this first determination are positive, one or more additional tests may be performed to confirm the presence of gastroparesis. Additional gastroparesis diagnostic tests with which the present methods may be used in conjunction include, but are not limited to: diagnostic tests based on symptoms and physical examination; diagnostic tests in which isotopic marker compositions are ingested and monitored, upper gastrointestinal endoscopy tests; antro-duodenal motility tests which measure the pressure that is generated by the contractions of the stomach and intestinal muscles; electrogastrograms (EGG) which record the electrical signals that travel through the stomach muscles and control the muscles' contractions; etc.

Where desired, methods of the invention may further include treating a subject for gastroparesis when the methods identify the subject as suffering from gastroparesis. Of interest are medications that treat gastroparesis by stimulating the stomach to contract more normally. Specific medications of interest include, but are not limited to: metoclopramide, domperidone, erythromycin, octreotide, etc. Where desired, surgery may be employed, such as surgery that creates a larger opening between the stomach and the small intestine in order to facilitate the process of emptying the stomach. Additional treatment protocols of interest include, but are not limited to those described in United States Published Application Nos. 20060029614; 20050164925; 20050106167; 20050090554; 20030059374 and 20020143030; the disclosures of which are herein incorporated by reference.

Other gastric motility disorders in which the methods of the invention find use include, but are not limited to: gastric dysrhythmias, such as bradygastria and tachygastria, and gastric outlet obstruction, pelvic floor dysfunction, chronic constipation, and GI conditions that are manifestations of diabetes and/or autonomic neuropathy. Other types of conditions in which electrogastrograms of the invention find use in the assessment thereof include, but are not limited to: other intestinal disorders, bladder disorders, Children with Angelman Syndrome, as well as endometriosis. Applications in which electrogastrograms of the invention find use are further reviewed in U.S. Pat. Nos. 5,704,368 and 6,351,665; as well as United States Published Application No. 20050215917; the disclosures of which are herein incorporated by reference. As described above, when methods of the invention are employed to assess such conditions, the methods may further include confirming diagnoses with one or more additional tests and/or treating the subject for the diagnosed condition with one or more treatment protocols.

In addition, electroviscerograms of the invention may find use in assessing physiological responses to various stimuli. In some instances, electrogastrograms of the invention may be employed to evaluate an individual's response to different types of foods. For example, observed electrogastrograms vary between high caloric content foods and low caloric content foods. Various in observed electrogastrograms may therefore be used to assess an individual's diet, e.g., where one wishes to monitor a subject's compliance with a dietary regimen.

Another type of gastrointestinal condition with which the subject methods find use is GERD, as well as related conditions, such as functional dyspepsia. Subjects of interest for these applications include those at least suspected of suffering from GERD. For assessment of GERD, one or more identifier units may be administered to a subject, where the identifier units are pH sensitive and are configured to emit a signal from which the pH at a given physiological site may be determined. Upon receipt of the signal or signals, an assessment of GERD may be obtained. For example, when a patient suffering from GERD is on a given treatment protocol, the methods of invention may be used to identify low gastric pH despite the treatment protocol that the patient is receiving. This result may be used to justify alteration of the treatment protocol in some manner. Alternatively, an identifier unit configured to provide a signal from which lower esophageal pH may be determined can be employed. With such an environmentally responsive identifier unit, low pH detected in the lower esophagus may be employed as a diagnostic marker of GERD.

Where desired, the methods of invention may be employed in conjunction with one or more additional GERD diagnostic methods. GERD diagnostic methods of interest include, but are not limited to: barium swallow X-rays, esophageal manometry, 24-hour esophageal pH monitoring and Esophagogastroduodenoscopy (EGD). The methods of invention may further include treating an individual for GERD following assessment of GERD by methods of the invention. Pharmacologic treatment protocols of interest include, but are not limited to: proton pump inhibitors (such as omeprazole, pantoprazole, lansoprazole, and rabeprazole); gastric H2 receptor blockers (such as ranitidine, famotidine and cimetidine); antacids; alginic acid; prokinetics (such as cisapride; sucralfate; 5-HT4 receptor agonists, such as mosapride citrate; etc.

It is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Certain ranges have been presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A system for detection of myoelectric activity, the system comprising:
    an ingestible identifier comprising:
        a housing including a first electrode and a second electrode secured thereto;
        a control unit electrically coupled to the first and second electrodes, wherein the control unit changes conductance between the first and second electrodes; and
        a detection unit electrically coupled to the first and second electrodes, wherein the detection unit reads a surrounding environment to collect information, wherein electrochemical reactions between the first electrode and the surrounding environment and the second electrode and the surrounding environment respectively produce a voltage potential that powers the ingestible identifier such that the control unit switches the ingestible identifier between broadcast mode and detection mode; and a second ingestible identifier configured to communicate with the ingestible identifier such that when the second ingestible identifier is in the broadcast mode the ingestible identifier is in the detection mode thereby allowing the ingestible identifiers to communicate.

2. The system of claim 1, wherein the information is encoded in a unique current signature produced by the ingestible identifier, wherein the information comprises identification information to indicate activation of the ingestible identifier.

3. The system of claim 2, wherein the information encoded in the ingestible identifier's unique current signature represents data gathered during the detection mode.

4. The system of claim 1, further comprising a receiver unit configured to communicate with at least one of the ingestible identifier or the second ingestible identifier.

5. The system of claim 4, wherein the receiver unit comprises a detection module capable of detecting low frequency current signals produced by a voltage potential and capable of detecting high frequency current signals produced by the ingestible identifier or the second ingestible identifier.

6. The system of claim 1, wherein the ingestible identifier further comprises a temperature sensing unit responsive to and capable of recording the surrounding temperature.

7. The system of claim 1, wherein the ingestible identifier includes a sensor capable of measuring the surrounding temperature.

8. The system of claim 1, wherein the ingestible identifier includes a sensor capable of measuring the surrounding pH level.

9. The system of claim 1, wherein the ingestible identifier measures acidic conditions and the second ingestible identifier measures alkaline conditions.

10. The system of claim 4, wherein the system further comprises an extra-corporeal data processor configured to receive data from the receiver unit and generate an electroviscerogram from the received data.

11. The system of claim 1, wherein the ingestible identifier includes a disc secured to the housing, wherein the disk is non-conducting, and wherein during the detection mode the ingestible identifier records data associated with myoelectric activity and during the broadcast mode the ingestible identifier produces a unique current signature including the data.

12. The system of claim 1, wherein during the detection mode the ingestible identifier detects and records data associated an implantable device and during the broadcast mode the ingestible identifier produces a unique current signature encoded with the data.

13. A system for creating an electroviscerogram for a subject based on detected myoelectric activity, the system comprising:

an ingestible identifier system with each ingestible identifier having at least two electrodes secured thereto for detection of a change in voltage potential associated with myoelectric information of the subject, the ingestible identifier system comprising:

an ingestible identifier comprising:
  a housing including a first electrode and a second electrode secured thereto,
  a control unit electrically coupled to the first and second electrodes, wherein the control unit changes conductance between the first and second electrodes;
  a detection unit electrically coupled to the first and second electrodes, wherein the detection unit reads a surrounding environment to collect information, wherein electrochemical reactions between the first electrode and the surrounding environment and the second electrode and the surrounding environment respectively produce the voltage potential that powers the ingestible identifier such that the control unit switches the ingestible identifier between broadcast mode and detection mode; and
  a processing unit for receiving the detected myoelectric information and providing an encoded message;
  a transmission module secured to the housing and electrically coupled to the processing unit, wherein the transmission module receives the encoded message from the processing unit; and
a second ingestible identifier configured to communicate with the ingestible identifier such that when the second ingestible identifier is in the detection mode, the ingestible identifier is in the broadcast mode thereby allowing the ingestible identifiers to communicate; and a decoding system comprising:
  a receiver module in communication with the transmission module, wherein the receiver module receives the transmitted encoded message and decides the transmitted encoded message to produce a decoded message; and
  a display module for receiving the decoded message and producing electroviscerogram.

14. The system of claim 13, wherein the ingestible identifier further comprises:
  a non-conducting membrane positioned between the first and second electrodes and secured to the housing.

15. The system of claim 13, wherein the ingestible identifier operated in the detection mode to gather information associated with an implanted pulse generator, and wherein during the broadcast mode the ingestible identifier produces a unique current signature containing the information associated with the implanted pulse generator.

16. The system of claim 13, wherein the ingestible identifier comprises a sensor that detects a physiological parameter and combines data associated with the physiological parameters with the data associated with myoelectric information and during the broadcast mode the ingestible identifier produces a unique current signature containing the combined information.

* * * * *